US008232251B2

(12) United States Patent
Hill et al.

(10) Patent No.: US 8,232,251 B2
(45) Date of Patent: *Jul. 31, 2012

(54) COMPOUNDS FOR DELIVERY OF THERAPEUTIC AND IMAGING MOIETIES TO NERVE CELLS

(75) Inventors: G. Craig Hill, Stockton, CA (US); Stephen B. Kahl, Portola Valley, CA (US); Robert R. Webb, Moss Beach, CA (US); Constance A. McKee, Woodside, CA (US)

(73) Assignee: Manzanita Pharmaceuticals, Inc., Woodside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/323,421

(22) Filed: Nov. 25, 2008

(65) Prior Publication Data

US 2009/0286732 A1 Nov. 19, 2009

Related U.S. Application Data

(63) Continuation of application No. 10/655,756, filed on Sep. 5, 2003, now abandoned, and a continuation-in-part of application No. 09/707,730, filed on Nov. 6, 2000, now Pat. No. 6,887,861, which is a continuation-in-part of application No. 09/217,037, filed on Dec. 21, 1998, now Pat. No. 6,652,864.

(60) Provisional application No. 60/409,127, filed on Sep. 5, 2002.

(51) Int. Cl.
*A61K 38/16* (2006.01)
*A61K 47/28* (2006.01)

(52) U.S. Cl. ...................... 514/21.2; 424/1.45
(58) Field of Classification Search .......... None
See application file for complete search history.

(56) References Cited

U.S. PATENT DOCUMENTS

| | | | |
|---|---|---|---|
| 5,389,623 A | 2/1995 | Bodor et al. | |
| 5,442,043 A | 8/1995 | Fukuta et al. | |
| 5,502,037 A | 3/1996 | Kondratyev | |
| 5,505,931 A | 4/1996 | Pribish | |
| 5,554,498 A | 9/1996 | Filler et al. | |
| 5,563,250 A | 10/1996 | Fitzner et al. | |
| 5,614,652 A | 3/1997 | Filler et al. | |
| 5,728,803 A | 3/1998 | Urfer et al. | |
| 5,767,288 A | 6/1998 | Stowell et al. | |
| 5,833,988 A | 11/1998 | Friden | |
| 5,948,384 A | 9/1999 | Filler | |
| 5,977,307 A | 11/1999 | Friden et al. | |
| 5,981,480 A | 11/1999 | Urfer et al. | |
| 5,989,545 A | 11/1999 | Foster et al. | |
| 5,990,078 A * | 11/1999 | Toran-Allerand | 514/8.3 |
| 6,486,303 B1 | 11/2002 | Moyle | |
| 6,503,728 B1 | 1/2003 | Urfer et al. | |
| 7,144,983 B1 | 12/2006 | Urfer et al. | |
| 7,528,233 B2 | 5/2009 | Urfer et al. | |

FOREIGN PATENT DOCUMENTS

| | | |
|---|---|---|
| WO | WO 93/10234 | 5/1993 |
| WO | WO 95/07092 | 3/1995 |
| WO | WO 95/32738 | 12/1995 |
| WO | WO 97/23608 | 3/1997 |
| WO | WO 97/21732 | 6/1997 |
| WO | WO 97/26275 | 7/1997 |
| WO | WO 97/37966 | 10/1997 |
| WO | WO 98/41220 | 9/1998 |
| WO | WO 99/21552 | 5/1999 |
| WO | WO 00/37103 | 6/2000 |
| WO | WO 01/91798 A2 | 12/2001 |

OTHER PUBLICATIONS

Sigma-aldrich (sigma-aldrich entry for fluocinolone acetonide retrieved from http://www.sigmaaldrich.com/catalog/ProductDetail.do?D7=0&N5=SEARCH_CONCAT_PNO%7CBRAND_KEY&N4=F8880%7CFLUKA&N25=0&QS=ON&F=SPEC on Feb. 17, 2011 2 pages).*
Moss ('IUPAC Nomenclature of steroids' v61 1989 Pure and Applied Chemistry pp. 1783-1822).*
Answers.com (Answers.com retrieved from http://wiki.answers.com/Q/Why_can_oxygen_only_form_2_bonds on Feb. 17, 2011 4 pages).*
Mclean et al ('Synthesis and pharmacological evaluation of conjugates of prednisolone and non-steroidal anti-inflammatory agents' Steroids 54/4 Oct. 1989 pp. 421-439).*
Toran-Allerand et al., "Cross-Coupling of Estrogen and Neurotrophin Receptor Systems in Developing Cerebral Cortex"; Internet. J. Develop. Neurosci. vol. 14, Suppl. 1, (1996), p. 99.
Agarwal, et al., "Effects of dexamethasone (DEX) on growth factor and neurotrophin mRNA expression by cultured human trabecular meshwork cells", IOVS (Mar. 15, 1999) vol. 40, No. 4, pp. S667 (Ann Mtg. of the Assoc for Research in Vision and Ophthalmology Fort Lauderdale, Florida, USA May 9-14, 1999).
Gonzalez, et al., "Glucocorticoid regulation of motoneuronal parameters in rats with spinal cord injury", Cellular and Molecular Neurobiology, (Oct. 1999) vol. 19, No. 5, pp. 597-611.
Nemoto, et al., "A possible mechanism of TPA-mediated downregulation of neurotrophin-3 gene expression in rat cultured vascular smooth muscle cells", Molecular Brain Research, (May 7, 1999) vol. 68, No. 1-2, pp. 186-189.
Smith, et al., "Regulation of NGFI-A (Egr-1) gene expression by the POU domain transcription factor Brn-3a", Brain Research, Molecular Brain Research, (Dec. 10, 1999) 74 (1-2) 117-25.

(Continued)

*Primary Examiner* — Cecilia J Tsang
*Assistant Examiner* — Ronald Niebauer
(74) *Attorney, Agent, or Firm* — Carol L. Francis; Bozicevic, Field & Francis LLP

(57) ABSTRACT

The invention features compounds of the general formula:

B-L-M where B is a binding agent capable of selectively binding to a nerve cell surface receptor and mediating absorption of the compound by the nerve cell; M is a moiety which performs a useful non-cytotoxic function when absorbed by a nerve cell, and can be a therapeutic moiety or an imaging moiety; and L is a linker coupling B to M. The invention also features methods of use of the compounds in, for example, treating conditions such as viral infections and pain, as well as in labeling nerve cells.

28 Claims, No Drawings

OTHER PUBLICATIONS

Shi, et al., "Dexamethasone induces hypertrophy of developing medial septum cholinergic neurons: potential role of nerve growth factor", Journal of Neuroscience, (Nov. 15, 1998) vol. 18, No. 22, pp. 9326-9334.

Binkley et al., "RNA Ligands to Human Nerve Growth Factor," Nucleic Aciods Research vol. 23 No. 16: pp. 3198-3205 (1995).

Fiume et al., "Galactosylated poly(L-lysine) as a Hepatotropic Carrier of 9-B-D-arabinofuranosyladenine 5'-monophosphate," FEBS 3810 vol. 203 No. 2: pp. 203-206 (Jul. 1986).

Haschke et al., "Preparation and Retrodrade Axonal Transport of an Antiviral Drug/Horseradish Peroxidase Conjugate," Journal of Neurochemistry vol. 35 No. 6: pp. 1431-1435 (Dec. 1980).

Kramer et al., "Monoclonal Antibody to Juman Trk-A: Diagnostic and Therapeutic Potential in Neuroblastoma," European Journal of Cancer vol. 33 No. 12: pp. 2090-2091 (Oct. 1997).

Li et al., "b-Endorphin Omission Analogs: Dissociation of Immunoreactivity from Other Biological Activities," Proc. Natl. Acad. Sci. USA 77(6): 3211-3214 (1980).

Maliartchouk et al., "Optimal Nerve Growth Factor Trphic Signals Mediated by Synergy of TrkA and p75 Receptor-Specific Ligands," Journal of Neuroscience vol. 17 No. 16: pp. 6031-6037 (1997).

Pardridge et al., "Transport of Human Recombinant Brain-Derived Neurotrophic Factor (BDNF) Through the Rat Blood-Brain Barrier in Vivo Using Vector-Mediated Peptide Drug Deliver," Pharmaceutical Research vol. 11 No. 5: pp. 746 (1994).

Ponzetto et al., "Adenine Arabinoside Monophosphate and Acuclovir Monophosphate Coupled to Lactosaminiated Albumin Reduce Woodchuck Hepatitis Virus Biremia at Doses Lower than do the Unconjugated Drugs," Hepatology vol. 14: pp. 16-24 (1991).

Schwab, M.E., "Ultrastructural Localization of a Nerve Growth Factor-Horseradish Peroxidase (NGF-HRP) Coupling Product after Retrograde Axonal Transport in Adreneric Neurons," Brain Research vol. 130 No. 1: pp. 190-196 (Jul. 8, 1977).

Schwab et al., "Labeled Wheat Germ Agglutinin (WGA) as a New, Highly Sensitive Retrograde Tracer in the Rat Brain Hippocampal System," Brain Research vol. 152 No. 1: pp. 145-150 (Aug. 18, 1978).

Schwab, et al., "Selective Retgrograde Transsynaptic Transfer of a Protein, Tetanus Toxin, Susequent to its Retrograde Axonal Transport," Journal of Cell Bilogy vol. 82 No. 3: pp. 798-810 (Sep. 1979).

Skolnick et al., "From Genes to Protein Structure and Function: Novel Applications of Computational Approaches in the Genomic Era," Trends in Biotechnolgoy vol. 18 No. 1: pp. 34-39 (2000).

Yang, et al., "Dexamethasone inhibits ischemia-induced transient reduction of neurotrophin-3 mRNA in rat hippocampal neurons", Neuroreport, (Oct. 26, 1998) vol. 9, No. 15, pp. 3477-3480.

Verity, et al., "Regulation of glial cell line-derived neurotrophic factor release from rat C6 blioblastoma cells", Journal of Neurochemistry, (Feb. 1998) vol. 70, No. 2, pp. 531-539.

Brandoli, et al., "Dexamethasone decreases P75NTR expression in injured spinal cord", Society for Neuroscience Abstracts, (1998) vol. 24, No. 1-2, pp. 290 ($28^{th}$ Ann Mtg. of the Society for Neuroscience, Part 1).

Prodanov, et al., "Pharmacology of apoptosis in the central nervous system", Farmatsiya, (Sofia) (1998), 45(2), 31-38.

Fink Jr., et al., "Effect of glucocorticoid on NGF-stimulated TRKA signaling in PC12 cells", Society for Neuroscience Abstracts, (1997) vol. 23, No. 1-2, pp. 1702 ($27^{th}$ Ann Mtg. of the Society for Neuroscience, New Orleans, Louisiana, USA Oct. 25-30, 1997).

Seidl, et al., "Expression of nerve growth factor and neurotrophin receptors in testicular cells suggest novel roles for neurotrophins outside the nervous system", Reproduction Fertility and Development, (1996) vol. 8, No. 7, pp. 1075-1087.

Barbany, "Modulation of neurotrophins and their receptors by adrenal steroids", CNS Neurotransmitters and Neuromodulators: Neuroactive Steroids (1996), 113-125.

Scully, et al, "Neuotrophin expression modulated by glucocorticoids and oestrogen in immortalized hippocampal neurons", Molecular Brain Research, (1995) vol. 31, No. 1-2, pp. 158-164.

Higaki, et al., "Neurotropin$^R$ inhibits lipopolysaccharide-induced nitric oxide production in cultured human endothelial cells", Cell structure and function, (1994) vol. 19, No. 6, pp. 555 ($47^{th}$ Ann Mtg. of the Japan Society for Cell Biology, Nagasaki, Japan, Sep. 28-30, 1994).

Kononen, et al., "Neurotropins and their receptors in the rat pituitary gland: regulation of BDNF and trk B mRNA levels by adrenal hormones", Molecular Brain Research, (1994) vol. 27, No. 2, pp. 347-354.

Lindholm, et al., "Glucocorticoids and neurotrophin gene regulation in the nervous system", Annals of the New York Academy of Sciences, (Nov. 30, 1994) 746, 195-202.

Jelsma, et al., "Different forms of the neurotrophin receptor trk B mRNA predominate in rat retina and optic nerve", Journal of Neurobiology, (1993) vol. 24, No. 9, pp. 1207-1214.

Barbany, et al., "Adrenalectomy attenuates kainic acid-elicited increases of messenger RNAs for neurotrophins and their receptors in the rat brain", Neuroscience, (1993) vol. 54, No. 4, pp. 909-922.

Cosi, et al., "Glucocorticoids depress activity-dependent expression of BDNF mRHA in hippocampal neurons", Neuroreport, (1993) vol. 4, No. 5, pp. 527-530.

Scully, et al., "Modulation of neurotrophin expression by glucocorticoids in immortalized hippocampal neurons", Society for Neuroscience Abstract, (1993) vol. 19, No. 1-3, pp. 256 ($23^{rd}$ Ann Mtg. of the Society for Neuroscience, Washington D.C., USA, Nov. 7-12, 1993).

Scully, et al., "glucocorticoid modulation of neurotrophin expression in immortalized mouse hippocampal neurons", Neuroscience Letters, (1993) vol. 155, No. 1, pp. 11-14.

Barbany, et al., "Regulation of Neurotrophin mRNA Expression in the rat brain by glucocorticoids", Eur J Neurosci, (1992) 4 (5) 396-403.

Wilcox, et al., "Characterization of Nerve Growth Factor-Dependent Herpes Simplex Virus Latency in Neurons in Vitro," Journal of Virology vol. 62 No. 2: pp. 393-399 (Feb. 1988).

* cited by examiner

COMPOUNDS FOR DELIVERY OF THERAPEUTIC AND IMAGING MOIETIES TO NERVE CELLS

CROSS-REFERENCE TO RELATED APPLICATIONS

This application is a continuation of U.S. application Ser. No. 10/655,756, filed Sep. 5, 2003, now abandoned, which application claims the benefit of provisional application Ser. No. 60/409,127, filed Sep. 5, 2002; and which application is a continuation-in-part U.S. application Ser. No. 09/707,730, now U.S. Pat. No. 6,887,861, filed Nov. 6, 2000, which is a continuation-in-part of U.S. application Ser. No. 09/217,037, now U.S. Pat. No. 6,652,864, filed Dec. 21, 1998, each of which is incorporated by reference in their entireties.

FIELD OF THE INVENTION

The present invention relates to compounds that can be used to deliver moieties selectively to nerve cells, and methods of use therefore. More specifically, the invention relates to compounds that can be used to deliver moieties, including therapeutic moieties and imaging moieties, selectively to sensory and motor neurons, and methods of use therefore.

BACKGROUND

Although our understanding of the structure and function of the nervous system has greatly advanced in recent years, a need still exists for efficacious treatments of many neurological disorders, including Alzheimer's disease, Parkinson's disease, Huntington's disease, schizophrenia, severe pain, multiple sclerosis, bipolar disease, and diseases of the nervous system caused by infection by viruses and other microorganisms (herpes simplex, HIV, cytomegalovirus, parasites, fungi, prions, etc.).

Many neuropharmaceutical agents have been developed to treat diseases of the nervous system, but their usefulness has been hampered by severe side effects partially due to nonspecific interactions between these agents and cells or tissues other than the targeted cells. For example, the corticosteroid hormone cortisone (4-pregnen-17α, 21-diol-3,11,20-trione) and its derivatives are widely used to treat inflammation in the body including the nervous system to reduce symptoms such as swelling, tenderness and pain. However, the steroid dosage has to be kept at the lowest effective level because of its severe side effects. Steroid hormones like cortisone bind to their cognate nuclear hormone receptors and induce a cascade of cellular effects, including programmed cell death of the neurons in the brain (Kawata et al., J. Steroid Biochem. Mol. Biol. 65: 273-280 (1998)). Since steroid hormone receptors, such as the glucocorticoid receptor for cortisone, are distributed in a wide variety of tissues and cells, nonspecific interactions of the hormone with its cognate receptor in different sites is unavoidable if the drug is circulated systemically.

A need thus continues to exist for an effective system for delivering therapeutic agents selectively to nerve cells and nerve tissues. Various techniques have been developed to deliver drugs selectively, but with only limited success.

For example, liposomes have been used as carrier molecules to deliver a broad spectrum of agents including small molecules, DNAs, RNAs, and proteins. Liposome mediated delivery of pharmaceutical agents has major drawbacks because of its lack of target specificity. Attempts have been made to overcome this problem by covalently attaching whole site-specific antibody or Fab fragments to liposomes containing a pharmaceutical agent (Martin et al., Biochem. 20, 4229-4238, (1981)). However, an intrinsic problem of particular importance in any liposome carrier system is that in most cases the targeted liposome does not selectively reach its target site in vivo. Whether or not liposomes are coated with antibody molecules, liposomes are readily phagocytosed by macrophages and removed from circulation before reaching their target sites.

SUMMARY OF THE INVENTION

The invention features compounds of the general formula:

$$B-L-M$$

where B is a binding agent capable of selectively binding to a nerve cell surface receptor and mediating absorption of the compound by the nerve cell; M is a moiety which performs a useful non-cytotoxic function when absorbed by a nerve cell, and can be a therapeutic moiety or an imaging moiety; and L is a linker coupling B to M. The invention also features methods of use of the compounds in, for example, treating conditions such as viral infections and pain, as well as in labeling nerve cells.

In certain embodiments, presently preferred, the binding agent is further capable of being transported retrogradely to the nerve cell body after internalization. In other particular embodiments, M is a therapeutic moiety (TM) or an imaging moiety (IM)

Thus, in one embodiment, the compounds have the general formula:

$$B-L-TM$$

where:

B is a binding agent capable of selectively binding to a nerve cell surface receptor and mediating absorption of the compound by the nerve cell;

TM is a therapeutic moiety which has a non-cytotoxic therapeutic effect when absorbed by a nerve cell; and L is a linker coupling B to TM.

And thus, in another embodiment, the compounds have the general formula:

$$B-L-IM$$

where:

B is a binding agent capable of selectively binding to a nerve cell surface receptor and mediating absorption of the compound by the nerve cell;

IM is a non-cytotoxic imaging moiety which can be used to image a nerve cell or an intracellular component of the nerve cell; and L is a linker coupling B to IM.

In regard to each of the above embodiments, particular classes of binding agents B which may be used include, but are not limited to, nucleic acid sequences, peptides, peptidomimetics, peptoids, antibodies and antibody fragments. As used herein, the term "peptides" includes polypeptides and oligopeptides of any length, and is generic to antibodies and antibody fragments.

Examples of nucleic acids that can serve as the binding agent B include, but are not limited to, DNA, RNA, and other nucleomimetic ligands that function as antagonists of nerve growth factors or inhibit binding of other growth factors to nerve cell surface receptors, such as aptamers that function as antagonists or nerve growth factors or inhibit binding of growth factors to nerve cell surface receptors.

Examples of peptides that can serve as the binding agent B include, but are not limited to, members of the nerve growth factor (neurotrophin) family such as NGF, BDNF, NT-3, NT-4, NT-6; derivatives (e.g., biochemically or chemically modified proteins having, for example, different glycosylation or other modification relative to a native protein), analogues (e.g., proteins that differ in amino acid sequence relative to an amino acid sequence of a native protein), and fragments of such nerve growth factors (e.g., a recombinant, naturally-occurring, or synthetic protein fragment or peptide or peptidomimetic that selectively binds a nerve growth factor receptor, e.g., recombinant molecules of NGF and BDNF); and synthetic peptides; where B selectively binds to a nerve cell surface receptor, and which may have agonist or antagonist activities of a nerve growth factor.

Antibodies, derivatives of antibodies and antibody fragments can also serve as the binding agent B. Examples of this type of binding agent B include, but are not limited to, anti-human trkA monoclonal antibody 5C3 and anti-human p75 monoclonal antibody MC192.

Where M is a therapeutic moiety, the therapeutic moiety TM is selected to perform a non-cytotoxic therapeutic function within nerve cells. Examples of non-cytotoxic functions which the therapeutic moiety TM may perform include, but are not limited to, the functions performed by adrenergic agents (agonist or antagonist) (e.g., epinephrine, norepinephrine, dopamine, atenolol), analgesics (e.g., opioids, morphine, codeine, oxycodone), anti-inflammatories (steroidal—e.g., cortisone, prednisolone, methylprednisolone, betamethasone, dexamethasone, and nonsteroidal—e.g., piroxicam, meclofenamate, etodolac), anti-trauma agents (e.g., adenosine, epinephrine, dopamine, epinephrine, and other agents used in the treatment of shock), anti-viral agents (e.g., acyclovir, ganciclovir, AZT, ddI, ddC, trifluridine, etc.), antibacterial and anti-infective agents, anti-arrthymic agents (e.g., adenosine), gene therapy agents (e.g., DNAs, RNAs, or other nucleomimetics which introduce a gene or replace a mutated gene), hormones (e.g., peptide hormones (e.g., growth factors) and steroid hormones ((e.g., cortisone, testosterone, progesterone, estrogen)), anti-oxidants, NMDA antagonists or modifiers, and immune system modulators, particularly those with antiviral activity such as interferons, etc.). In general, the therapeutic moiety is not a nerve growth factor.

Examples of classes of therapeutic moieties include, but are not limited to, adrenergic agents (e.g., epinephrine, norepinephrine, dopamine, atenolol), analgesics (e.g., opioids, morphine, codeine, oxycodone), anti-inflammatories (steroidal—e.g., prednisolone, methylprednisolone, betamethasone, dexamethasone and nonsteroidal—e.g., piroxicam, meclofenamate, etodolac) anti-trauma agents, anti-viral agents (e.g., acyclovir, ganciclovir, AZT, ddI, ddC, trifluridine, etc.), gene therapy agents (e.g., DNAs, RNAs, or nucleomimetics which introduce a gene or replace a mutated gene), steroids (e.g., pregnanes, estranes, and androstanes, such as corticosteroids, including cortisone, progestins, such as progesterone, and estranes, such as estradiol), and nonsteroidal hormones (e.g., growth factors); and immune system modulators, such as interferons, etc.). Exemplary therapeutic moieties of interest are described in more detail below.

Where M is an imaging moiety (IM), IM is a non-cytotoxic agent that can be used to determine whether a nerve cell or an internal component of the nerve cell is specifically associated with (e.g., has absorbed) the imaging moiety, and optionally locate and, further optionally, visualize, such nerve cells or nerve cell internal components. For example, fluorescent dyes may be used as an imaging moiety IM. In another example, radioactive agents that are non-cytotoxic may also be an imaging moiety IM. In some embodiments, the IM is a moiety other than horse radish peroxidase (HRP). In other embodiments, the imaging moiety provides a detectable signal that does not require the addition of a substrate for detection.

In one embodiment, the IM is a charged moiety. Cells have difficulty transporting charged molecules across cell membranes. According to this embodiment, the binding agent B serves to facilitate transport of a charged imaging moiety IM into a cell. Within the cell, the compound (i.e. the conjugate formed between B and IM) is metabolized to form a metabolite product that comprises the charged imaging moiety IM. The metabolite product is less prone to being transported across the cell membrane out of the cell relative to the conjugate because of the metabolism of the conjugate resulting in the separation of the imaging moiety IM from the binding agent B. The metabolite product is also less prone to being transported across the cell membrane out of the cell relative to a non-charged version of the imaging moiety due to the charge that the imaging moiety carries.

According to this embodiment, compounds are provided which comprise a charged imaging moiety, the charged derivative being conjugated to a binding agent (also interchangeably referred to herein as a "binding moiety") B that facilitates transport of the IM across a cell membrane into a cell, the cell metabolizing at least a portion of the imaging agent to form a charged metabolite product that provides for a detectable signal, the charged metabolite product being less prone to being transported across the cell membrane out of the cell relative to the conjugate and less prone to being transported across the cell membrane out of the cell relative to an uncharged imaging agent.

In one particular embodiment, the charged imaging moiety IM is Alexa Fluor 488®, Molecular Probes, a fused heterocyclic 3 ring aromatic system with a pendant phenyl ring with an amino, a quaternary amine, two sulfonic acid lithium salts, a carboxylic acid, and one carboxylic acid N-hydroxy-succinimidyl ester groups attached. It is this last group that forms an amide crosslink to the epsilon amino group of lysine. This compound is a highly modified derivative of the imaging moiety fluorescein with very similar absorption and emission spectra but with a much higher extinction coefficient. In another embodiment, the charged imaging moiety IM is a similarly modified derivative of Texas Red® but of proprietary makeup, Alexa Fluor 647®, Molecular Probes.

In general, the linker may be any moiety that can be used to link the binding agent B to the moiety M. In one particular embodiment, the linker is a cleavable linker. The use of a cleavable linker enables the moiety M linked to the binding agent B to be released from the compound once absorbed by the nerve cell and transported to the cell body. The cleavable linker may be cleavable by a chemical agent, by an enzyme, due to a pH change, or by being exposed to energy. Examples of forms of energy that may be used include light, microwave, ultrasound, and radiofrequency.

In certain applications, it is desirable to release the moiety M, particularly where M is a therapeutic moiety TM, once the compound has entered the nerve cell, resulting in a release of the moiety M. Accordingly, in one variation, the linker L is a cleavable linker. This enables the moiety M to be released from the compound once absorbed by the nerve cell. This may be desirable when, for example, M is a therapeutic moiety TM which has a greater therapeutic effect when separated from the binding agent. For example, the therapeutic moiety TM may have a better ability to be absorbed by an intracellular component of the nerve cell when separated from the binding agent. Accordingly, it may be necessary or desirable to separate the therapeutic moiety TM from the compound so that the therapeutic moiety TM can enter the intracellular compartment.

The present invention also relates to a method for selectively delivering a moiety into nerve cells comprising the steps of:

delivering to a patient a compound having the general formula:

B-L-M where:
B is a binding agent capable of selectively binding to a nerve cell surface receptor and mediating absorption of the compound by the nerve cell;
M is a moiety which performs a useful non-cytotoxic function when absorbed by a nerve cell; and
L is a linker coupling B to M,
having the compound selectively bind to a nerve cell surface receptor via the binding agent B; and
having the compound be absorbed by the nerve cell mediated by the binding of the binding agent B to the nerve cell surface receptor.

In one embodiment, moiety M is a therapeutic moiety TM as described herein and in another embodiment is an imaging moiety IM.

The above method can be used to deliver therapeutic moieties for treating a variety of neurological disorders when the therapeutic moiety TM is a moiety useful for treating such neurological disorders.

The above method can be used to deliver therapeutic moieties for treating pain when a therapeutic moiety TM for treating pain, such as an analgesic or anti-inflammatory, is included as the therapeutic moiety TM in the compound.

The above method can also be used to deliver steroid hormones for treating nerve damage when a therapeutic moiety TM for treating nerve damage, such as a steroid hormone, is included as the therapeutic moiety TM in the compound.

The above method can also be used to stimulate nerve growth when a therapeutic moiety TM for inducing the production of a nerve growth factor is included as the therapeutic moiety TM in the compound.

The above method can also be used to treat infected nerve cells infected with viruses or immunize nerve cells from viruses when the therapeutic moiety TM in the compound is an antiviral agent.

The above method can also be used to perform gene therapy when the therapeutic moiety TM is a gene therapy agent.

The present invention also relates to a method for improving intracellular administration of a therapeutic agent, by administration of a B-L-TM compound of the invention.

In one embodiment, this method is used in conjunction with the conjugates of the present invention and hence is used in conjunction with the methods of the present invention for selectively delivering a moiety into nerve cells.

DETAILED DESCRIPTION OF THE INVENTION

The present invention relates to compounds which include a binding agent that binds to a nerve cell surface receptor and facilitates absorption of the compound by the nerve cell; and a moiety. Different moieties may be included in the compounds of the present invention including therapeutic moieties that are non-cytotoxic to the nerve cells and imaging moieties that can be used to image nerve cells that absorb these compounds.

In one embodiment, compounds of the present invention have the general formula:

B-L-M where:
B is a binding agent capable of selectively binding to a nerve cell surface receptor and mediating absorption of the compound by the nerve cell;
M is a moiety, which can be a therapeutic moiety TM which has a non-cytotoxic therapeutic effect when absorbed by a nerve cell, or an imaging moiety IM which provides for detectable labeling of a nerve cell; and
L is a linker coupling B to TM.

According to this embodiment, the binding agent B serves as a homing agent for nerve cells by selectively binding to nerve cell surface receptors. The binding agent B also serves to facilitate absorption of the compound by the nerve cell. In certain embodiments, presently preferred, binding agent B is retrogradely transported to the cell body.

The binding agent B can be any molecule that can perform the first two, and preferably the third, of these functions. Particular classes of binding agents which may be used include, but are not limited to, nucleic acid sequences, peptides, peptidomimetics, antibodies and antibody fragments. Further exemplary binding agents are described in detail below.

The linker L serves to link the binding agent B to the moiety M. A wide variety of linkers are known in the art for linking two molecules together, particularly, for linking a moiety to a peptide or nucleic acid, all of which are included within the scope of the present invention.

Examples of classes of linkers that may be used to link the binding agent B to the moiety M include amide, alkylamine, carbamate, phosphoramide, ester, ether, thioether, alkyl, cycloalkyl, aryl, and heteroaryl linkages such as those described in Hermanson, G. T., Bioconjugate Techniques (1996), Academic Press, San Diego, Calif.

In certain applications, it is desirable to release the moiety M, particularly where M is a therapeutic moiety TM, once the compound has entered the nerve cell, resulting in a release of the moiety M. Accordingly, in one variation, the linker L is a cleavable linker. This enables the moiety M to be released from the compound once absorbed by the nerve cell. This may be desirable when, for example, M is a therapeutic moiety TM which has a greater therapeutic effect when separated from the binding agent. For example, the therapeutic moiety TM may have a better ability to be absorbed by an intracellular component of the nerve cell when separated from the binding agent. Accordingly, it may be necessary or desirable to separate the therapeutic moiety TM from the compound so that the therapeutic moiety TM can enter the intracellular compartment.

Cleavage of the linker releasing the therapeutic moiety may be as a result of a change in conditions within the nerve cells as compared to outside the nerve cells, for example, due to a change in pH within the nerve cell. Cleavage of the linker may occur due to the presence of an enzyme within the nerve cell that cleaves the linker once the compound enters the nerve cell. Alternatively, cleavage of the linker may occur in response to energy or a chemical being applied to the nerve cell. Examples of types of energies that may be used to effect cleavage of the linker include, but are not limited to light, ultrasound, microwave and radiofrequency energy.

In one embodiment, compounds of the present invention have the general formula:

B-L-TM where:
B is a binding agent capable of selectively binding to a nerve cell surface receptor and mediating absorption of the compound by the nerve cell;
TM is a therapeutic moiety which has a non-cytotoxic therapeutic effect when absorbed by a nerve cell; and
L is a linker coupling B to TM.

In another embodiment, compounds of the present invention have the general formula:

B-L-IM where:
B is a binding agent capable of selectively binding to a nerve cell surface receptor and mediating absorption of the compound by the nerve cell;
IM is a non-cytotoxic imaging moiety which can be used to image the nerve cell or an intracellular component of the nerve cell; and
L is a linker coupling B to IM.

According to this embodiment, the binding agent B and linker L may be varied as described above with regard to compounds having the general formula B-L-TM. Further according to this embodiment, the imaging moiety IM may be a non-cytotoxic moiety which can be used to image nerve cells. Examples of imaging moieties that may be used include fluorescent dyes, radioisotopes and other detectable moieties such as luminophores which are non-cytotoxic.

The present invention also relates to a method for selectively delivering a non-cytotoxic therapeutic moiety into nerve cells comprising the steps of:

delivering to a patient a therapeutic amount of a compound having the general formula:

B-L-TM where:

- B is a binding agent capable of selectively binding to a nerve cell surface receptor and mediating absorption of the compound by the nerve cell,
- TM is a therapeutic moiety which has a non-cytotoxic therapeutic effect when absorbed by a nerve cell, and
- L is a linker coupling B to TM;

having the compound selectively bind to a nerve cell surface receptor via the binding agent B; and having the compound be absorbed by the nerve cell mediated by the binding of the binding agent B to the nerve cell surface receptor.

The method of the present invention offers the advantage of specifically targeting a non-cytotoxic therapeutic moiety to nerve cells where the therapeutic moiety is absorbed by the nerve cells. The method utilizes the fact that internalization of the conjugated agent is mediated by the binding of the binding agent B to nerve cell surface receptors. Once internalized, the therapeutic moiety can accumulate within the nerve cells where it has a therapeutic effect. In certain embodiments, the compound of the present invention is transported retrogradely to the cell body after internalization; in such cases, the therapeutic moiety can accumulate within the nerve cell body.

The ability to deliver the compound selectively to nerve cells reduces the overall amount of therapeutic moiety that needs to be administered. Selective delivery of the therapeutic moiety to the nerve cell reduces the amount of side effects observed due to non-specific administration of the therapeutic moiety. In addition, the therapeutic moiety is less likely to be separated from the binding agent and non-specifically administered as compared to delivery methods involving the use of a binding agent and a therapeutic moiety in combination. Various and exemplary applications of the conjugates of the invention having a therapeutic moiety are described below.

The method of the present invention can be used to deliver therapeutic moieties for treating a variety of neurological disorders including, but not limited to, Alzheimer's disease, Parkinson's disease, multiple sclerosis, neurodegenerative disease, epilepsy, seizure, migraine, trauma and pain. Examples of neuropharmaceuticals that may be used include proteins, antibiotics, adrenergic agents, anticonvulsants, analgesics, anti-inflammatories, anti-viral agents, gene therapy agents, hormones (growth factors), and immune system modulators, particularly those with antiviral activity such as interferons, nucleotide analogues, anti-trauma agents, peptides and other classes of agents used to treat or prevent a neurological disorders. For example, analgesics such as opioids, morphine, codeine, and oxycodone can be conjugated to the binding agent B and specifically delivered to the nerve cells. Since the same level of pain relief can be achieved using a smaller dosage of analgesics, side effects such as respiratory depression or potential drug addiction can be avoided or at least ameliorated.

Steroid hormones such as corticosteroids can also be conjugated with nerve cell-specific binding agents and used to treat inflammation of the nerves, which may reduce the side effects associated with high doses of steroids, such as weight gain, redistribution of fat, increase in susceptibility to infection, and avascular necrosis of bone. Corticosteroids include, inter alia, cortisol (4-pregnen-11,17,21-triol-3,20-dione), cortisone (4-pregnen-17,21-diol-3,11,20-trione), deoxycorticosterone (4-pregnen-21-hydroxy-3,20-dione), prednisone (1,4-pregnadien-17α,21-diol-3,11,20-trione), prednisolone (1,4-pregnadiene-11β, 17α,21-triol-3,20-dione), methylprednisolone (1,4-pregnadiene-6α-methyl-11β, 17α,21-triol-3,20-dione), beclomethasone (1,4-pregnadiene-9-chloro-11β,17,21-triol-16β-methyl-3,20-dione-17,21-dipropionate), triamcinolone (1,4-pregnadiene-9-fluoro-11β, 16α, 17,21-tetrahydroxy-3,20-dione) and its derivative triamcinolone acetonide, (1,4-pregnadiene-9-fluoro-11β, 16α, 17,21-tetrahydroxy-3,20-dione cyclic 16,17-acetal with acetone), desonide (1,4-pregnadiene-3,20-dione, 11β,21-dihydroxy-16α, 17-[(1-methylethylidene)bis(oxy)]), alclometasone (typically as the dipropionate: 1,4-pregnadiene-7a-chloro-11β,17,21-trihydroxy, 16α-methyl, 3,20-dione, 17,21-dipropionate), flurandrenolide (4-pregnene-3,20-dione, 6α-fluoro-11β, 21-dihydroxy-16α, 17-[(1-methylethylidene)bis(oxy)]), dexamethasone (1,4-pregnadiene-9-fluoro-11β,17,21-trihydroxy-16α-methyl, 3,20-dione), desoximetasone (1,4-pregnadiene-3,20-dione,9-fluoro-11β, 21-dihydroxy-16α-methyl), flumethasone (1,4-pregnadiene-3,20-dione-9α-fluoro-16α-methyl-11β,17,21-trihydroxy), and betamethasone (1,4-pregnadiene, 9-Fluoro-1,16,17,21-trihydroxy-16β-methyl-3,20-dione) and its derivatives (such as the dipropionate: 1,4-pregnadiene, 9-Fluoro-1,16,17,21-trihydroxy-16β-methyl-3,20-dione 17,21-dipropionate).

The method according to the present invention can also be used to deliver agents that induce the production of nerve growth factor in the target nerve cells, especially under conditions of pathogenic under-expression of NGFs (See Riaz, S. S. and Tomlinson, D. R. Prog. Neurobiol. 49: 125-143 (1996)). NGF induction has been demonstrated in a wide variety of cell types, such as fibroblasts (Furukawa, Y et al., FEBS Lett. 247: 463-467 (1989)), astrocytes (Furukawa, Y. et al., FEBS Lett. 208: 258-262 (1986)), Schwann cells (Ohi, T. et al., Biochem. Int. 20:739-746 (1990)) with a variety of agents including cytokines, steroids, vitamins, hormones, and unidentified components of serum. Specific examples of agents known to induce NGF include 4-methylcatechol, clenbuterol, isoprenaline, L-tryptophan, 1,25-dihydroxyvitamin D3, forskolin, fellutamide A, gangliosides and quinone derivatives (Riaz, S. S. and Tomlinson, D. R. Prog. Neurobiol. 49: 125-143 (1996)).

The method according to the present invention can also be used to deliver antiviral drugs into nerve cells in order to treat diseases caused by viral infection, to eliminate viruses spread to the nerves, and to inhibit infection by such viruses. Examples of viruses that infect the nervous system include but are not limited to rabies viruses, herpes viruses, polioviruses, arboviruses, reoviruses, pseudorabies, corona viruses, and Borna disease viruses. For example, antiviral drugs such as acyclovir, ganciclovir, cidofovir, and trifluridine can be conjugated to the binding agent and used to inhibit active or latent herpes simplex viruses in the peripheral and central nervous system. Specific delivery of the conjugate containing these antiviral drugs to the nervous system can reduce the side effects associated with high doses or long-term administration of these drugs, such as headaches, rash and paresthesia. The method according to the present invention can also be used to deliver marker compounds to image intracellular components of the nerve cells. Such marker compounds include but are not limited to fluorescent dyes, radioactive compounds, and other luminophores.

The method according to the present invention can also be used to perform gene therapy wherein nucleic acids (DNA, RNA or other nucleomimetics) are delivered to the nerve cells. These nucleic acids may serve to replace genes that are either defective, absent or otherwise not properly expressed by the patient's nerve cell genome.

The above and other features and advantages of the present invention will become more apparent in the following description of the preferred embodiments in greater detail.

1. Binding Agent (B)

According to the present invention, a compound with a binding agent B is used to selectively deliver the conjugated M, which can be a therapeutic moiety TM or an imaging moiety IM, to nerve cells. At the surface of the nerve cell, the binding agent B interacts with a receptor expressed on the nerve cell and is absorbed by the nerve cell mediated by this interaction. Any molecules possessing these two physical properties are intended to fall within the scope of a binding agent B as it is used in the present invention. In particular, peptides or proteins with these features can serve as a binding agent B, examples including but not limited to nerve growth factors (neurotrophins), antibodies against nerve cell-specific surface proteins, mutants and synthetic peptides derived from these peptides or proteins.

In one embodiment, neurotrophins are preferably used as the binding agent B. Neurotrophins are a family of small, basic polypeptides that are required for the growth, development and survival of neurons. A particular "survival" factor is taken up by the neuron via binding to one or more of a related family of transmembrane receptors. Table I lists several members of the neurotrophin family and their cognate receptors. The neurotrophin from which the binding agent is derived may be of any suitable origin, e.g., human, mouse. Where the conjugate is to be delivered to a human, the neurotrophin is preferably a human neurotrophin.

As listed in Table 1, nerve growth factor (NGF) is the first identified and probably the best characterized member of the neurotrophin family. It has prominent effects on developing sensory and sympathetic neurons of the peripheral nervous system. Brain-derived neurotrophic factor (BDNF) has neurotrophic activities similar to NGF, and is expressed mainly in the CNS and has been detected in the heart, lung, skeletal muscle and sciatic nerve in the periphery (Leibrock, J. et al., Nature, 341:149-152 (1989)). Neurotrophin-3 (NT-3) is the third member of the NGF family and is expressed predominantly in a subset of pyramidal and granular neurons of the hippocampus, and has been detected in the cerebellum, cerebral cortex and peripheral tissues such as liver and skeletal muscles (Ernfors, P. et al., Neuron 1: 983-996 (1990)). Neurotrophin-4 (also called NT-4/5) is the most variable member of the neurotrophin family. Neurotrophin-6 (NT-6) was found in teleost fish and binds to p75 receptor.

As listed in Table 1 at least two classes of transmembrane glycoproteins (trk and p75) have been identified which serve as endogenous receptors for neurotrophins. The trk receptors (tyrosine kinase-containing receptor) bind to neurotrophins with high affinity, whereas the p75 receptors possess lower affinity for neurotrophins. For example, nerve growth factor (NGF) binds to a relatively small number of trkA receptors with high affinity ($K_D=10^{-11}$) and to more abundant p75 with lower affinity ($K_D=10^{-9}$). The receptor-bound NGF is internalized with membrane-bound vesicles and retrogradely transported to the neuronal cell body. Thus, native neurotrophins, or fragments or other modified form of neurotrophins, can serve as the binding agent B in the compound according the present invention to deliver the conjugated moiety M to the neuronal cell body whether it be a therapeutic moiety, TM, or an imaging moiety, IM.

TABLE 1

The Neurotrophin Family and Its Receptors.

| | Receptor | | Responsive neurons |
|---|---|---|---|
| Factor | Kinase isoforms | Nonkinase forms | (examples) |
| NGF | TrkA | p75 | Cholinergic forebrain neurons<br>Sympathetic ganglia<br>DRG nociceptive |
| BDNF | TrkB | $p75^{LNTR}$<br>$trkB_{T1}$<br>$trkB_{T2}$ | Many CNS populations<br>Vestibular ganglia<br>Nodose ganglia<br>DRG mechanoreceptors |
| NT-3 | TrkC<br>trkB and trkA<br>Nonpreferred | $p75^{LNTR}$<br>$trkC_{TK-113}$<br>$trkC_{TK-108}$ | Many CNS populations<br>Cochlear ganglia<br>DRG proprioceptive |
| NT-4 | TrkB | p75<br>$trkB_{T1}$<br>$trkB_{T2}$ | Many CNS populations<br>Nodose ganglia<br>Petrosalganglia |
| NT-6 | TrkA | p75 | |

Thus specific examples of peptides that can serve as the binding agent B include, but are not limited to, members of the nerve growth factors (neurotrophin) family such as nerve growth factor (NGF), brain-derived neurotrophic factor (BDNF), neurotrophin-3 (NT-3), neurotrophin-4 (NT-4), neurotrophin-6 (NT-6), etc. (see reviews: Frade, J. M., et al., Bioessays 20: 137-145 (1998); Shieh, P. B., Curr. Biol. 7: R627-R630 (1997); Dechant, G., et al., Curr. Opin. Neurobiol. 7: 413-418 (1997); Chao, M. V. and Hempstead, B. L., Trends Neurobiol. 18: 321-326 (1995)); and derivatives, analogues, and fragments of nerve growth factors such as recombinant molecules of NGF and BDNF (Ibanez et al., EMBO J. 10: 2105-2110; Ibanez et al., EMBO J. 12: 2281-2293), synthetic peptides that bind to nerve cell surface receptors and have agonist or antagonist activities of nerve growth factors (Longo, F. M., et al., Cell Regulation 1: 189-195 (1990); LeSauteur, L. et al., J. Biol. Chem. 270: 6564-6569 (1995); Longo F. M., et al., J. Neurosci. Res. 48: 1-17; Longo, et al., Nature Biotech. 14: 1120-1122 (1997)).

In addition to the neurotrophins described above, analogues and derivatives of neurotrophins may also serve as the binding agent B. The structure of mouse NGF has been solved by X-ray crystallography at 2.3 Å resolution (McDonald et al., Nature, 345: 411-414, (1991)). Murine NGF is a dimeric molecule, with 118 amino acids per protomer. The structure of the protomer consists of three antiparallel pairs of beta strands that form a flat surface, four loop regions containing many of the variable residues between different NGF-related molecules, which may determine the different receptor specificities, and a cluster of positively charged side chains, which may provide a complementary interaction with the acidic low-affinity NGF receptor. Murine NGF has a tertiary structure based on a cluster of three cysteine disulfides and two extended, but distorted beta-hairpins. One of these β-hairpin loops was formed by the NGF 29-35 region.

Structure/function relationship studies of NGF and NGF-related recombinant molecules demonstrated that mutations in NGF region 25-36, along with other β-hairpin loop and non-loop regions, significantly influenced NGF/NGF-receptor interactions (Ibanez et al., EMBO J., 10, 2105-2110, (1991)). Small peptides derived from this region have been demonstrated to mimic NGF in binding to trkA receptor and affecting biological responses (LeSauteur et al. J. Biol. Chem. 270, 6564-6569, 1995). Dimers of cyclized peptides corresponding to β-loop regions of NGF were found to act as partial NGF agonists in that they had both survival-promoting and NGF-inhibiting activity while monomer and linear peptides were inactive (Longo et al., J. Neurosci. Res., 48, 1-17, 1997). Cyclic peptides have also been designed and synthesized to mimic the β-loop regions of NGF, BDNF, NT3 and NT-4/5. Certain monomers, dimers or polymers of these cyclic peptides may have a three-dimensional structure which binds to neurotrophin receptors under physiological conditions. All of these structural analogues of neurotrophins that bind to nerve cell surface receptors and are internalized can serve as the binding agent B of the compound according to the present invention to deliver the conjugated therapeutic moiety TM to the nervous system.

Alternatively, peptidomimetics (or "peptide mimics") that are synthesized by incorporating unnatural amino acids or other organic molecules may serve as the binding agent B of the compound according to the present invention to deliver the conjugated therapeutic agent TM into the nerve cells. Peptide mimetics are thus generally non-naturally occurring analogues of a peptide which, because of protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon-carbon bond or an acyl bond).

Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. Additionally, substitution of D-amino acids for the normal L-stereoisomer can be effected, e.g. to increase the half-life of the molecule. These synthetic peptide mimics are capable of binding to the nerve cell surface receptor and being internalized into the cell.

Other binding moieties B suitable for use in the invention include peptoids of nerve growth factors and antibodies that specifically bind a nerve cell surface receptor. Peptoids are protein-like molecules that contain an unnatural imino acids (see, e.g., Simon, R. J. et al. (1992) Proc. Natl. Acad. Sci. USA 89:9367-9371) containing N-substituted glycine residues wherein the substituents on the nitrogen atom are the alpha-position side chains of amino acids. Because they are amino acids that do not occur in nature, peptoid residues or peptides containing peptoid residues have higher resistance to enzymatic attacks. In recent years, peptoid residues have been widely used in the design and synthesis of drugs and other peptide related biomaterials.

Alternatively, antibodies against nerve cell surface receptors that are capable of binding to the receptors and being internalized can also serve as the binding agent B. For example, monoclonal antibody (MAb) 5C3 is specific for the NGF docking site of the human p140 trkA receptor, with no cross-reactivity with human trkB receptor. MAb 5C3 and its Fab mimic the effects of NGF in vitro, and image human trk-A positive tumors in vivo (Kramer et al., Eur. J. Cancer, 33, 2090-2091, (1997)). Molecular cloning, recombination, mutagenesis and modeling studies of MAb 5C3 variable region indicated that three or less of its complementarity determining regions (CDRs) are relevant for binding to trkA. Assays with recombinant CDRs and CDR-like synthetic polypeptides demonstrated that they had agonistic bioactivities similar to intact MAb 5C3. Monoclonal antibody MC192 against p75 receptor has also been demonstrated to have neurotrophic effects.

Thus antibodies, derivatives of antibodies and antibody fragments that can serve as the binding agent B include, but are not limited to, anti-human trkA monoclonal antibody 5C3 (Kramer, K., et al., Eur. J. Cancer 33: 2020-2091 (1997)), anti-human p75 monoclonal antibody MC192 (Maliatchouk, S. and Saragovi, H. U., J. Neurosci. 17: 6031-7) and fragments and derivatives thereof that retain antigen binding. Such can serve as the binding agent B of the compound according to the present invention to deliver the conjugated moiety M to or into the nerve cells.

It is noted that the identification and selection of moieties that can serve as binding agents in the present invention can be readily performed by attaching an imaging moiety IM to the potential binding agent in order to detect whether the potential binding agent is internalized by the nerve cells. In this regard, combinatorial and mutagenesis approaches may be used to identify analogues, derivatives and fragments of known binding moieties which may also be used as binding moieties according to the present invention.

The position of the linker within the binding agent is selected so as to maintaining the ability of the binding agent to bind to the desired nerve cell surface receptor. In general, it is preferred that the residue to which the linker is attached is one that is outside of the area of the protein that binds to the corresponding receptor. For example, where the binding agent is NGF or BDNF, the second most exposed lysine at residue 95 is within the TrkA binding site, and thus is less preferred for attachment of a linker. In some embodiments where the binding agent B is NGF or BDNF, it may be most desirable to attach the linker to the lysine corresponding to the most exposed lysine residue at position 74 of the native NGF or native BDNF protein.

In general, the binding agent is linked to at least one moiety via a linker. Normally, and particularly where the binding agent is a neurotrophin (e.g., NGF, BDNF, NT-3, NT-4), the binding agent has only one linker, and dimers of the conjugated binding agents have two linker-moiety constructs attached.

2. Moiety (M)

As noted above, the binding agent B is conjugated to a moiety M, which may be either a non-cytoxic therapeutic moiety (TM) or an imaging moiety (IM).

Therapeutic Moiety (TM)

An aspect of the present invention relates to the delivery of compounds into nerve cells that are non-cytotoxic to the nerve cells and perform a therapeutic function. Examples of therapeutic functions include, but are not limited to, treatment of neurological disorders, gene therapy, intracellular target imaging, cell sorting, or separation schemes. In general, the therapeutic moiety is not a nerve growth factor.

Examples of classes of therapeutic moieties include, but are not limited to adrenergic agents such as epinephrine, norepinephrine, dopamine, atenolol; analgesics such as opioids, morphine, codeine, oxycodone; anti-trauma agents; anti-inflammatories (steroidal—e.g., prednisolone, methylprednisolone, betamethasone, dexamethason and nonsteroidal—e.g., piroxicam, meclofenamate, etodolac); anti-viral agents such as acyclovir, ganciclovir, trifluridine, AZT, ddI, ddC, trifluridine, and the like; gene therapy agents (e.g., DNAs, RNAs, or nucleomimetics which introduce a gene or replace a mutated gene); and hormones, including steroidal hormones (e.g., pregnanes, estranes, androstanes, and specifically corticosteroids, including cortisone, cortisone (4-pregnen-17α, 21-diol-3,11,20-trione), progestins (e.g., progesterone), estrogen, and estranes, such as estradiol) and non-steroidal hormones, such as growth factors; and interferons. Such compounds may optionally also include an imaging moiety, such as fluorescent moieties, or proteins, a luminophore; or radioactive labels, for imaging intracellular components of the nerve cells.

Examples of neuropharmaceuticals that may be used as, or adapted for use as, therapeutic moieties include proteins, antibiotics, adrenergic agents, anticonvulsants, analgesics, anti-inflammatories, nucleotide analogues, anti-trauma agents, peptides and other classes of agents used to treat or prevent a neurological disorders. For example, analgesics such as opioids, morphine, codeine, and oxycodone can be conjugated to the binding agent B and specifically delivered to the nerve cells. Since the same level of pain relief can be achieved using a smaller dosage of analgesics, side effects such as respiratory depression or potential drug addiction can be avoided or at least ameliorated. Such can find particular use as therapeutic moieties in treatment of a variety of neurological disorders including, but not limited to, Alzheimer's disease, Parkinson's disease, multiple sclerosis, neurodegenerative disease, epilepsy, seizure, migraine, trauma and pain.

In one embodiment, the therapeutic moiety is a steroid hormone or derivative thereof. As noted above, such find use in, for example, treatment of inflammation of the nerves, which may reduce the side effects associated with high doses of steroids, such as weight gain, redistribution of fat, increase in susceptibility to infection, and avascular necrosis of bone. Corticosteroids contemplated by the invention include, inter alia, cortisol (4-pregnen-11,17,21-triol-3,20-dione), cortisone (4-pregnen-17,21-diol-3,11,20-trione), deoxycorticosterone (4-pregnen-21-hydroxy-3,20-dione), prednisone (1,4-pregnadien-17α,21-diol-3,11,20-trione), prednisolone (1,4-pregnadiene-11β,17α,21-triol-3,20-dione), methylprednisolone (1,4-pregnadiene, 9-Fluoro-1,16,17,21-trihydroxy-16β-methyl-3,20-dione), beclomethasone (1,4-pregnadiene-9-chloro-11β,17,21-triol-16β-methyl-3,20-dione-17,21-dipropionate), triamcinolone (1,4-pregnadiene-9-fluoro-11β, 16α,17,21-tetrahydroxy-3,20-dione), triamcinolone acetonide (1,4-pregnadiene-9-fluoro-11β, 16α,17,21-tetrahydroxy-3,20-dione cyclic 16,17-acetal with acetone), desonide (1,4-pregnadiene-3,20-dione,11β,21-dihydroxy-16α,17-[(1-methylethylidene)bis(oxy)], alclometasone (typically as the dipropionate: 1,4-pregnadiene-7a-chloro-11β,17,21-trihydroxy, 16α-methyl, 3,20-dione, 17,21-dipropionate), flurandrenolide (4-pregnene-3,20-dione, 6α-fluoro-11β,21 dihydroxy-16α,17-[(1-methylethylidene)bis(oxy)]), dexamethasone (1,4-pregnadiene-9-fluoro-11β,17,21-trihydroxy-16α-methyl, 3,20-dione), desoximetasone (1,4-pregnadiene-3,20-dione,9-fluoro-11β, 21-dihydroxy-16α-methyl), flumethasone (1,4-pregnadiene-3,20-dione-9α-fluoro-16α-methyl-11β,17,21-trihydroxy), and betamethasone (1,4-pregnadiene, 9-Fluoro-1,16,17,21-trihydroxy-16β-methyl-3,20-dione) and its derivatives (such as the diprionate: 1,4-pregnadiene, 9-Fluoro-1,16,17,21-trihydroxy-16β-methyl-3,20-dione 17,21-dipropionate).

Further therapeutic moieties for use in the conjugates include moieties that induce the production of nerve growth factor in the target nerve cells, especially under conditions of pathogenic under-expression of NGFs (See Riaz, et al. Prog. Neurobiol. 49: 125-143 (1996)). NGF induction has been demonstrated in a wide variety of cell types, such as fibroblasts (Furukawa, et al., FEBS Lett. 247: 463-467 (1989)), astrocytes (Furukawa, et al., FEBS Lett. 208: 258-262 (1986)), Schwann cells (Ohi, et al., Biochem. Int. 20:739-746 (1990)) with a variety of agents including cytokines, steroids, vitamins, hormones, and unidentified components of serum. Specific examples of agents known to induce NGF, and thus specifically contemplated as therapeutic moieties in the present invention, include 4-methylcatechol, clenbuterol, isoprenaline, L-tryptophan, 1,25-dihydroxyvitamin D3, forskolin, fellutamide A, gangliosides and quinone derivatives (Riaz, et al. Prog. Neurobiol. 49: 125-143 (1996)).

In one embodiment of particular interest, the therapeutic moiety is an antiviral agent. Conjugates of the invention having an antiviral agent as a therapeutic moiety can be used to treat diseases or symptoms caused by or associated with viral infection, to eliminate viral spread to the nerves, and to inhibit infection by such viruses. For example, antiviral drugs such as acyclovir, ganciclovir, cidofovir, and trifluridine can be conjugated to the binding agent and used to inhibit active or latent herpes simplex viruses in the peripheral and central nervous system. Specific delivery of the conjugate containing these antiviral drugs to the nervous system can reduce the side effects associated with high doses or long-term administration of these drugs, such as headaches, rash and paresthesia.

The Table immediately below provides exemplary classes, and exemplary compounds within the classes, of therapeutic moieties that can be used or adapted for use in the conjugates of the invention.

Table of Exemplary Therapeutic Moieties

Antivirals

Acyclovir
Enviroxime
Ganciclovir
Lamivudine (3TC)
Trifluridine
Zidovudine (AZT)
Steroidal Anti-
inflammatories Betamethasone
Dexamethasone -continued Table of Exemplary Therapeutic Moieties Flumethasone
Fluocinolone Acetonide
Methylprednisolone
Prednisolone
Steroid Hormones Cortisone
Estradiol
Progesterone
Testosterone
Non-Steroidal Anti-
inflammatories Celecoxib
Etodolac
Meclofenamate
Piroxicam
Analgesics Buprenorphine
Butorphanol
Etorphine
Levorphanol
Morphine
Naltrexone
Oxymorphone
Na+/K+/Ca++ Channel
Blockers Baclofen
Gabapentin
Mexilitine
Procaine
Propoxycaine
Anti-bacterials/infectives Ceftriaxone
Eflornithine
Minocycline
Pentamidine
NMDA
Antagonists/Modifiers Amantadine
Dextromethorphan
Ketamine
Phenformin
Adrenergic agents Dopamine
Epinephrine
Phentolamine
Tranylcypromine
Mitochondrial modifiers Creatine
Creatine Phosphate
Anti-oxidants N-Acetyl-Cysteine
Tauroursodeoxycholic Acid
Anti-arrthymic Adenosine
Mexilitine
Other Compounds DNA oligomer - Antisense
Hyoscyamine -
Anticholinergic
N-Acetyl-Aspartic Acid -
Myelin Lipid Acylator
WHI-P131 - Jak3 inhibitor Further examples of therapeutic agents suitable for use, or suitable to be adapted for use, in the conjugates of the invention are described in the Tables below.

Imaging Moiety (IM)

The method according to the present invention can also be used to deliver marker compounds to identify, detect, and, optionally, locate or visualize, a nerve cell or an internal component of the nerve cell. Such is accomplished by specific binding of the binding moiety B to the nerve cell and, in some embodiments, internalize or absorb, the imaging moiety of the conjugate. Imaging moieties of interest include but are not limited to fluorescent dyes or proteins, a lumniphore; or radioactive labels. In general, IM is not horse radish peroxidase (HRP). In one embodiment, the imaging moiety that provides a detectable signal that does not require the addition of a substrate for detection.

A further aspect of the present invention relates to compositions and methods for improving the intracellular delivery of a imaging agent to a cell, particularly a nerve cell using a charged imaging moiety in the conjugate. According to this embodiment, the binding agent B facilitates transport of a charged imaging moiety IM into a cell. Within the cell, the compound (i.e. the conjugate formed between B and IM) is metabolized to form a metabolite product that comprises the charged imaging moiety IM. The charged metabolite product is less prone to being transported across the cell membrane out of the cell relative to a non-charged version of the imaging moiety.

In one particular embodiment, the charged imaging moiety IM is Alexa Fluor 488®, Molecular Probes, a fused heterocyclic 3 ring aromatic system with a pendant phenyl ring with an amino, a quaternary amine, two sulfonic acid lithium salts, a carboxylic acid, and one carboxylic acid N-hydroxy-succinimidyl ester groups attached. It is this last group that forms an amide crosslink to the epsilon amino group of lysine. This compound is a highly modified derivative of the imaging moiety fluorescein with very similar absorption and emission spectra but with a much higher extinction coefficient. In another embodiment, the charged imaging moiety IM is a similarly modified derivative of Texas Red® but of proprietary makeup, Alexa Fluor 647®, Molecular Probes.

Also according to this embodiment, methods are provided which comprise administering an imaging agent to a cell, or to a subject, in a form where the imaging agent comprises a charge and is conjugated to a protein that acts as a binding moiety to facilitate transport of the conjugate across a cell membrane into a cell. Once within the cell, the cell metabolizes at least a portion of the compound to form a metabolite product that has the detectable properties of the imaging agent. The metabolite product is less prone to being transported across the cell membrane out of the cell relative to the compound, because of the metabolism of the compound resulting separation of the imaging moiety from the protein, and is less prone to being transported across the cell membrane out of the cell relative to an uncharged version of the imaging moiety.

This method may be used in conjunction with the conjugates of the present invention for selectively delivering a moiety to nerve cells. However, it is noted that charged imaging moieties can be used with binding agents that target cells other than nerve cells.

3. Linker (L)

According to the present invention, a binding agent B is linked to a moiety M by a linker L. In general, any method of linking a binding agent to a therapeutic moiety may be used and is intended to fall within the scope of the present invention. The linker L generally serves to link the binding agent B to the therapeutic moiety TM. A wide variety of linkers are known in the art for linking two molecules together, particularly, for linking a moiety to a peptide or nucleic acid, all of which are included within the scope of the present invention.

Examples of classes of linkers that may be used to link the binding agent B to the therapeutic moiety TM include amide, alkylamine, carbamate, phosphoramide, ester, ether, thioether, alkyl, cycloalkyl, aryl, and heteroaryl linkages such as those described in Hermanson, G. T., Bioconjugate Techniques (1996), Academic Press, San Diego, Calif.

Many different types of linkers have been developed for cross linking proteins and conjugating proteins or peptides with other agents. These linkers include zero-length cross linkers, homobifunctional cross-linkers, heterobifunctional cross-linkers and trifunctional cross-linkers. These linkers may have different susceptibility to cleavage under certain conditions. Depending on a particular application according to the present invention, an appropriate linker may be chosen. When an intracellular release of the agent from its conjugate is desired, a cleavable linker is chosen which is susceptible to cleavage by external stimuli such as light and heat, by intracellular enzymes, or by a particular microenvironment inside the cell.

In one embodiment, the linker L has one of the following general structures:

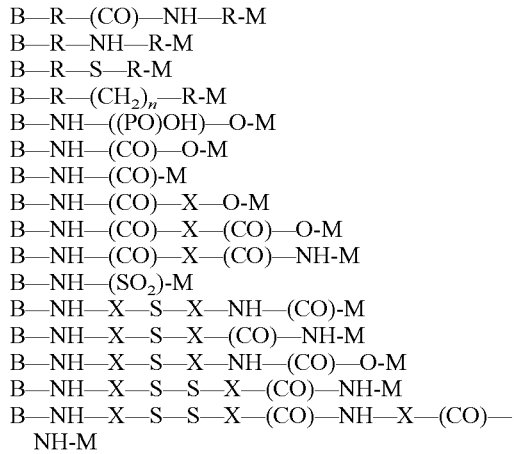

B—R—(CO)—NH—R-M
B—R—NH—R-M
B—R—S—R-M
B—R—(CH$_2$)$_n$—R-M
B—NH—((PO)OH)—O-M
B—NH—(CO)—O-M
B—NH—(CO)-M
B—NH—(CO)—X—O-M
B—NH—(CO)—X—(CO)—O-M
B—NH—(CO)—X—(CO)—NH-M
B—NH—(SO$_2$)-M
B—NH—X—S—X—NH—(CO)-M
B—NH—X—S—X—(CO)—NH-M
B—NH—X—S—X—NH—(CO)—O-M
B—NH—X—S—S—X—(CO)—NH-M
B—NH—X—S—S—X—(CO)—NH—X—(CO)—NH-M wherein R and X are each independently chosen from an alkyl, a heteroalkyl, an alkene, a heteroalkane, an aryl, a heteroaryl, a cycloalkyl, a heterocycloalkyl, a cycloalkene or a heterocycloalkene.

4. Cleavable Linkers

One particular embodiment of the present invention relates to compounds that include a cleavable linker L, which cleavable linker may be used to join a binding agent with either a therapeutic moiety or an imaging moiety. Use of a cleavable linker may be more desirable where, for example, the therapeutic moiety TM is more efficacious or potent when free from a carrier molecule such as a binding agent. In such instances, it is desirable to utilize a cleavable linker which allows the therapeutic moiety TM to be released from the compound once inside the cell.

Many cleavable linker groups have been developed which are susceptible to cleavage and by a wide variety of mechanisms. For example, linkers have been developed which may be cleaved by reduction of a disulfide bond, by irradiation of a photolabile bond, by hydrolysis of derivatized amino acid side chain, by serum complement-mediated hydrolysis, and by acid-catalyzed hydrolysis.

For example, cleavage of the linker releasing the therapeutic moiety may be as a result of a change in conditions within the nerve cells as compared to outside the nerve cells, for example, due to a change in pH within the nerve cell. Cleavage of the linker may occur due to the presence of an enzyme within the nerve cell that cleaves the linker once the compound enters the nerve cell. Alternatively, cleavage of the linker may occur in response to energy or a chemical being applied to the nerve cell. Examples of types of energies that may be used to effect cleavage of the linker include, but are not limited to light, ultrasound, microwave and radiofrequency energy.

Preferably, the linker used is one that, following conjugate production, links the binding agent B and the moiety M by only an amide or a carbamate bond. Furthermore, it is also preferred that the linker, upon cleavage following delivery into the nerve cell, provides for a binding agent product and a moiety product that is either modified only by the addition of a carboxylic acid group or not modified relative to the binding agent or moiety prior to conjugation (e.g., cleavage of the linker provides the "native" starting materials of the binding agent and moiety prior to conjugation, or the "native" starting material modified only by addition of a carboxylic acid group). Use of such linkers also provides that cleavage may results in production of carbon dioxide as the by-product. This embodiment thus provides the advantage of reduced cytotoxicity of the products of conjugate cleavage in the nerve cell.

The linker L used to link the binding agent B to the therapeutic moiety TM may be a photolabile linker. Examples of photolabile linkers include those linkers described in U.S. Pat. No. 5,767,288 and No. 4,469,774.

Acid-labile linkers are preferred in the practice of the present invention by taking advantage of a cell's receptor-mediated endocytosis pathways. Receptors that are internalized by receptor-mediated endocytosis pass through acidified compartments known as endosomes or receptosomes. Since the interior of the endosomal compartment is kept acidic (pH~6.0) by ATP-driven H$^+$ pumps in the endosomal membrane that pump H$^+$ into the lumen from the cytosol, a change in pH within the nerve cell can be used to cause the acid-labile linker to be cleaved and release the moiety.

Thus, in one embodiment of particular interest, the linker L used to link the binding agent B to the moiety M, particularly where the moiety is a therapeutic moiety TM, is an acid labile linker. Examples of acid labile linkers include linkers formed by using cis-aconitic acid, cis-carboxylic alkatriene, polymaleic anhydride, and other acid labile linkers, such as those linkers described in U.S. Pat. Nos. 5,563,250 and 5,505,931.

Further examples of cleavable linkers include, but are not limited to the linkers described in Lin, et al., J. Org. Chem. 56:6850-6856 (1991); Ph.D. Thesis of W.-C. Lin, U. C. Riverside, (1990); Hobart, et al., J. Immunological Methods 153: 93-98 (1992); Jayabaskaran, et al., Preparative Biochemistry 17(2): 121-141 (1987); Mouton, et al., Archives of Biochemistry and Biophysics 218: 101-108 (1982); Funkakoshi, et al., J. of Chromatography 638:21-27 (1993); Gildea, et al., Tetrahedron Letters 31: 7095-7098 (1990); WO 85/04674; and Dynabeads® (Dynal, Inc., 5 Delaware Drive, Lake Success, N.Y. 11042).

5. Examples of Compounds According to the Present Invention

In one embodiment, the compound of the present invention is a conjugated 4-pregnen-21-hydroxy or 1,4-pregnadiene-21-hydroxy steroid, wherein the conjugant group pends from the steroid 21 hydroxyl group and comprises a neurotrophin or a neurotrophin receptor-binding fragment thereof. Conjugated steroids such as described above may have, for example, a 21-carbamate linkage to the conjugant group, or a 21-phosphoramide linkage to the conjugant group. The neurotrophin or neurotrophin fragment may pend covalently, for example, through a lysine residue epsilon amino group or through a thiolated lysine residue epsilon amino group.

The conjugated 4-pregnen-21-hydroxy or 1,4-pregnadiene-21-hydroxy steroid may be a conjugated corticosteroid such as cortisone, prednisolone, methylprednisolone, betamethasone, dexamethasone, flumethasone, triamcinolone acetonide, or fluocinolone acetonide.

The neurotrophin may be, for example, NGF, BDNF, NT-3, NT-4, or NT-6, or a receptor-binding fragment or derivative thereof.

The neurotrophin fragment may be, for example, an NGF fragment capable of binding to trkA receptors and being internalized therewith. In certain embodiments, the NGF fragment is capable of binding to trkA receptors, being internalized therewith, and then being retrogradely transported to the nerve cell body.

In other embodiments, the compound may be a conjugated 4-pregnen-21-hydroxy or 1,4-pregnadiene-21-hydroxy steroid, wherein the conjugant group pends from the steroid 21 hydroxyl group and comprises BDNF or a BDNF fragment or derivative that is capable of binding to trkB receptors and being internalized therewith, optionally additionally being retrogradely transported to the cell body therewith.

In a further embodiment, the compound may comprise triamcinolone acetonide conjugated by a 21-carbamate linkage to NGF, or to a receptor-binding fragment of NGF, which pends covalently through a lysine residue epsilon amino group. In another embodiment, the compound may comprise fluocinolone acetonide conjugated by a 21-carbamate linkage to NGF, a receptor-binding fragment of NGF, BDNF, a receptor-binding fragment of BDNF, or another neurotrophin or receptor-binding fragment thereof, which pends covalently through a lysine residue epsilon amino group.

Table 2 provides several compounds according to the present invention. It is noted that in each instance, the particular therapeutic moieties, binding moieties, and linkers shown may be interchanged with other suitable therapeutic moieties, binding moieties, and linkers. In this regard, the compounds shown in the table are intended to illustrate the diversity of compounds provided according to the present invention.

TABLE 2

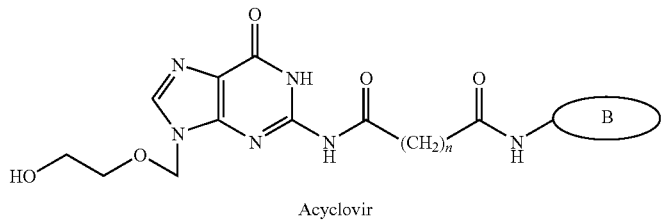

Acyclovir wherein B is selected from the group consisting of nerve growth factors, NGF, BDNF, NT-3, NT-4, NT-6, and anti-neurotrophin receptor antibodies MAb 5C3 and MAb MC192.

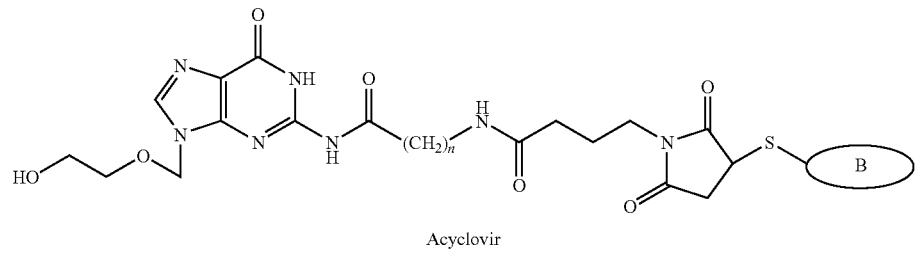

Acyclovir wherein B is selected from the group consisting of nerve growth factors NGF, BDNF, NT-3, NT-4, NT-6, anti-neurotrophin receptor antibodies MAb 5C3 and MAb MC192.

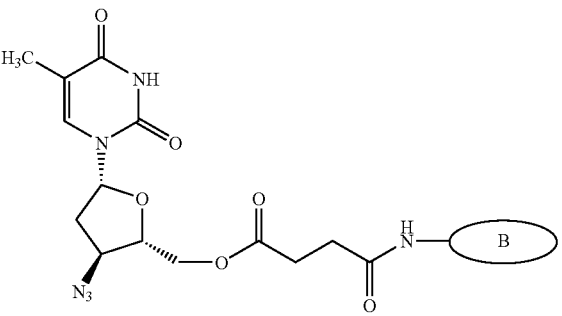

AZT wherein B is selected from the group consisting of nerve growth factors NGF, BDNF, NT-3, NT-4, NT-6, anti-neurotrophin receptor antibodies MAb 5C3 and MAb MC192.

TABLE 2-continued

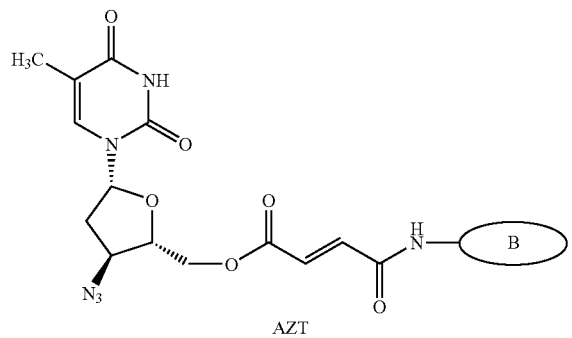

AZT
wherein B is selected from the group consisting of nerve growth factors NGF, BDNF,
NT-3, NT-4, NT-6, anti-neurotrophin receptor antibodies MAb 5C3 and MAb MC192.

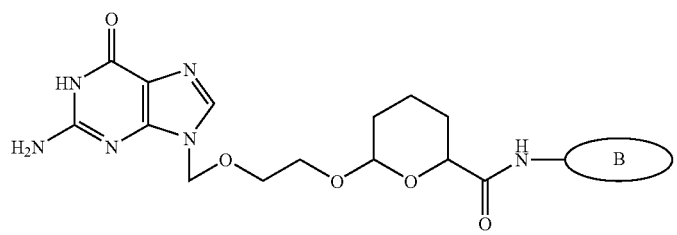

Acyclovir
wherein B is selected from the group consisting of nerve growth factors NGF, BDNF,
NT-3, NT-4, NT-6, anti-neurotrophin receptor antibodies MAb 5C3 and MAb MC192.

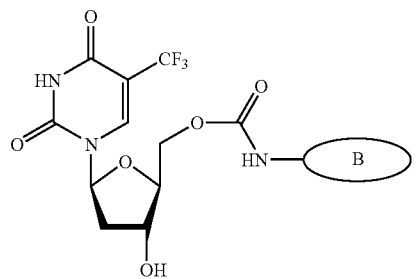

Trifluridine
wherein B is selected from the group consisting of nerve growth factors NGF, BDNF,
NT-3, NT-4, NT-6, anti-neurotrophin receptor antibodies MAb 5C3 and MAb MC192.

6. Examples of Compounds for Treating Pain

Table 3 provides several therapeutic moieties which may be used in the compounds and methods of the present invention for treating pain. It is noted that any of the various binding moieties and linkers described herein may be employed with these therapeutic agents. Indicated in the table below as * are reactive groups presently preferred for attaching linkers to the therapeutic moieties.

7. Examples of Linkers

Table 4 provides a series of linkers for linking different therapeutic moieties and binding moieties together. As illustrated, linkers are provided for attaching moieties that have thiol (—SH), hydroxyl (—OH), carboxylic acid (—COOH), sulfonic acid (—SO3H) and amino (—NH2) groups to the linkers. In these examples, neurotrophin is shown as the binding agent. However, it is noted that neurotrophin can be substituted with other binding moieties described herein, and other linkers can be substituted for the linkers in the exemplary compounds below. These compounds provided below are intended to be exemplary only, and not limiting.

TABLE 3

Pain - Steroidal anti-inflammatory agents

Betamethasone (1,4-pregnadien-9α-fluoro-11β,
17α, 21-triol-16β methyl-3,20-dione)

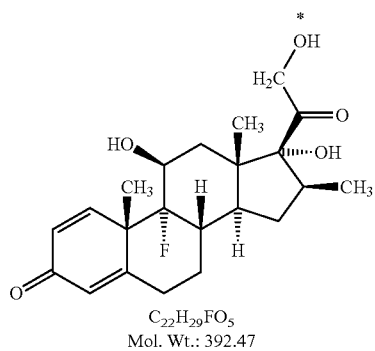

$C_{22}H_{29}FO_5$
Mol. Wt.: 392.47

TABLE 3-continued

Dexamethasone (1,4-pregnadien-9α-fluoro-11β, 17α, 21-triol-16α methyl-3,20-dione)

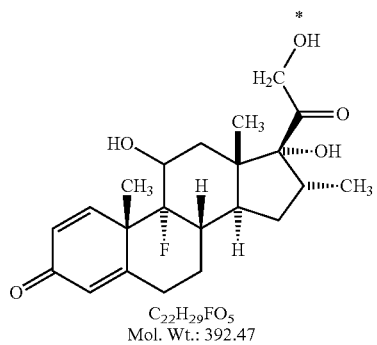

$C_{22}H_{29}FO_5$
Mol. Wt.: 392.47

Triamcinolone acetonide (1,4-pregnandien-9α-fluoro-11β, 16α, 17α, 21-tetrol 3,20-dione 16,17-acetonide)

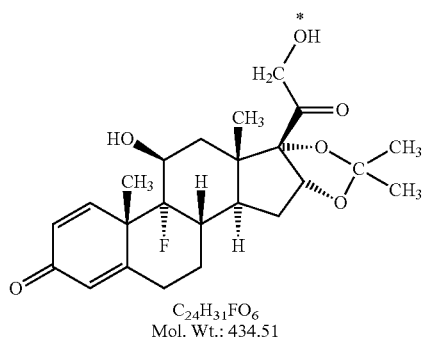

$C_{24}H_{31}FO_6$
Mol. Wt.: 434.51

Fluocinolone acetonide ({(6α, 11β, 16α)-1,4-pregnadiene-6,9-difluoro-11,21-dihydroxy-16,17[(1-methylethylidene)bis(oxy)]-3,20-dione, cyclic 16,17 acetal with acetone})

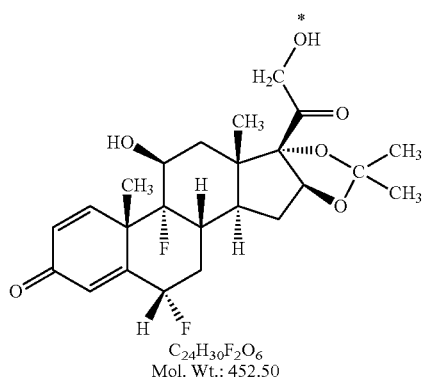

$C_{24}H_{30}F_2O_6$
Mol. Wt.: 452.50

Pain - Non-steroidal anti-inflammatory agent

Piroxicam

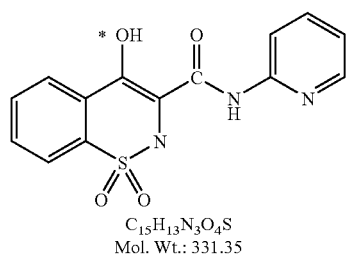

$C_{15}H_{13}N_3O_4S$
Mol. Wt.: 331.35

Pain - Local anesthetic agents

Propoxycaine

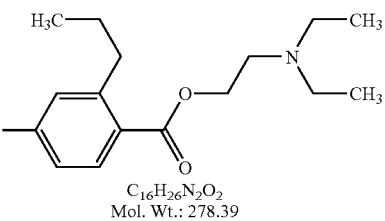

$C_{16}H_{26}N_2O_2$
Mol. Wt.: 278.39

Pain - Narcotic Agonists

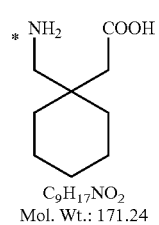

Morphine

Pain - Channel blockers

Gabapentin

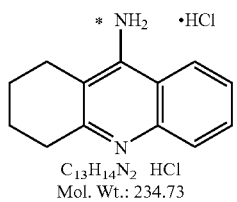

$C_9H_{17}NO_2$
Mol. Wt.: 171.24

Anti-neurodegenerative

Tacrine HCl

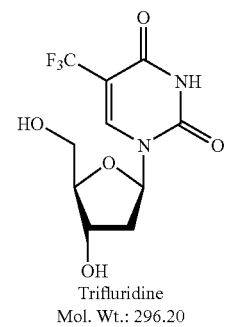

$C_{13}H_{14}N_2$ · HCl
Mol. Wt.: 234.73

Antiviral

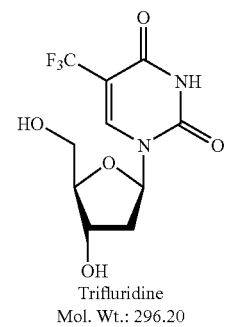

Trifluridine
Mol. Wt.: 296.20

TABLE 3-continued
Cidofovir
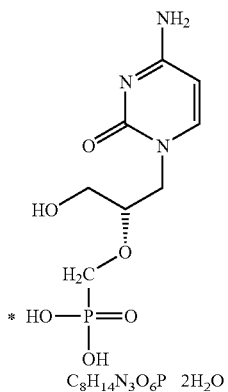
$C_8H_{14}N_3O_6P$ · $2H_2O$
Mol. Wt.: 315.22
Trifluridine conjugate
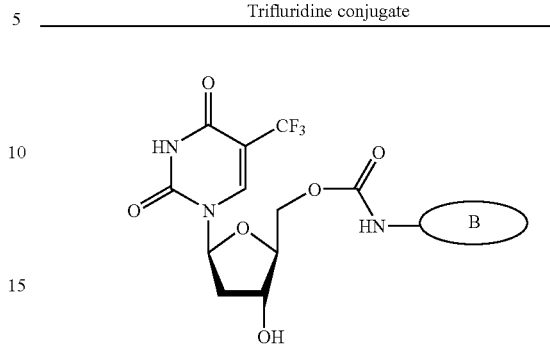
TABLE 4
Hydroxyl group conjugations
e.g., Steroids, Piroxicam, Acyclovir, Morphine
PMPI
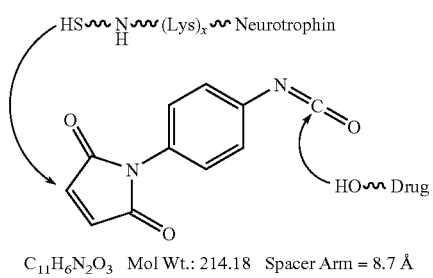
$C_{11}H_6N_2O_3$   Mol Wt.: 214.18   Spacer Arm = 8.7 Å
Amino group conjugations
e.g., Propoxycaine, Gabapentin, Tacrine
LC-SPDP
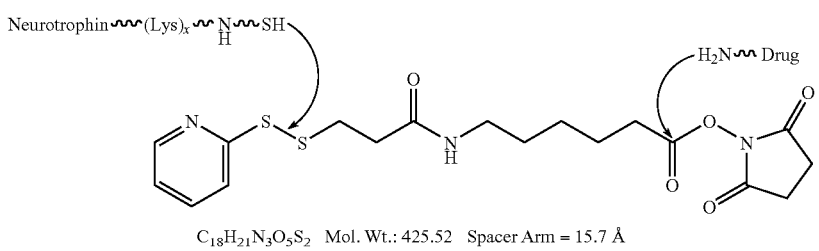
$C_{18}H_{21}N_3O_5S_2$   Mol. Wt.: 425.52   Spacer Arm = 15.7 Å
Sulfo-LC-SMPT
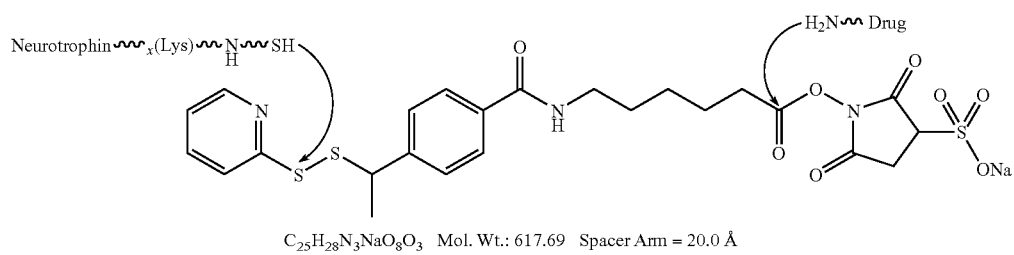
$C_{25}H_{28}N_3NaO_8O_3$   Mol. Wt.: 617.69   Spacer Arm = 20.0 Å

TABLE 4-continued
SMPT
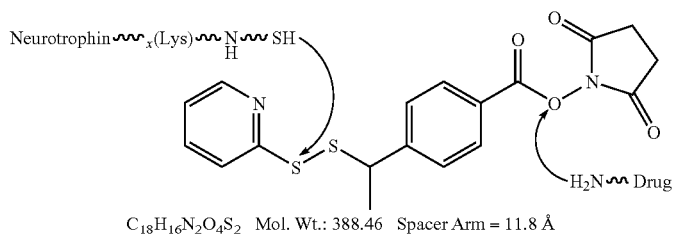
$C_{18}H_{16}N_2O_4S_2$ Mol. Wt.: 388.46 Spacer Arm = 11.8 Å
Phosphate group conjugations
Imidazolide Linker acyclovir-monophosphate (ACV-MP)
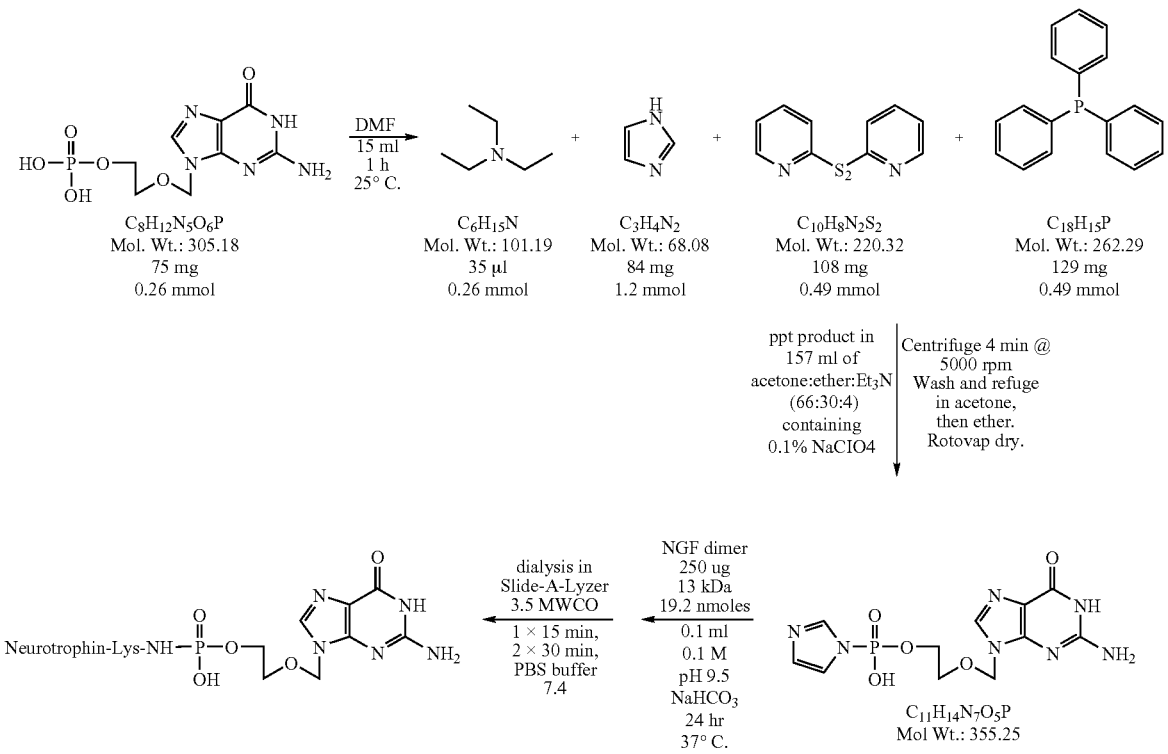
8. Synthetic Sequence for Attaching Acyclovir to NGF Via PMPI
Illustrated below is a synthetic sequence for the attachment of acyclovir to NGF via the linker PMPI.
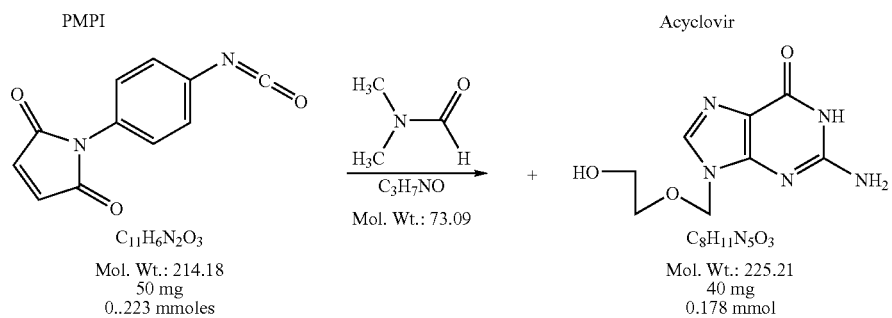

-continued
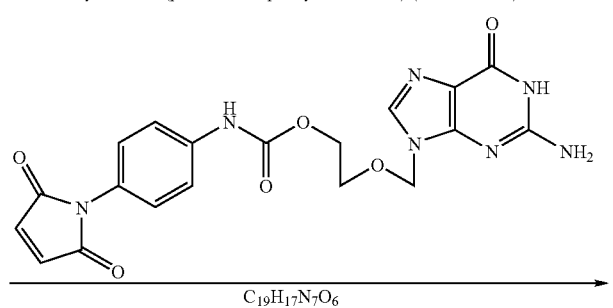
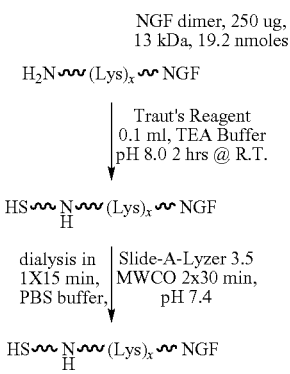
9. Synthetic Sequence for Attaching Acyclovir to NGF Via Imidazole
Illustrated below is a synthetic sequence for the attachment of acyclovir to NGF via an imidazole linker.
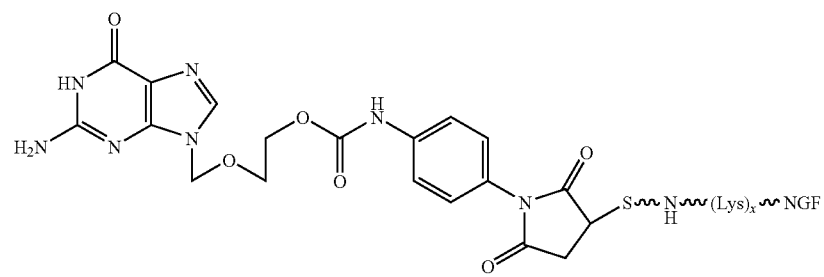
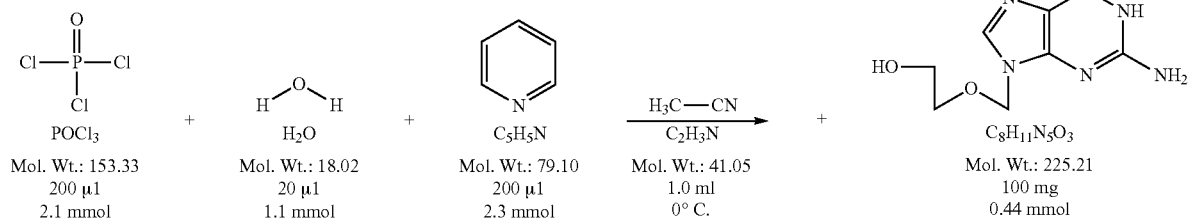
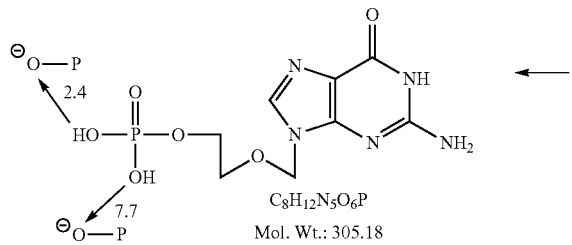

-continued

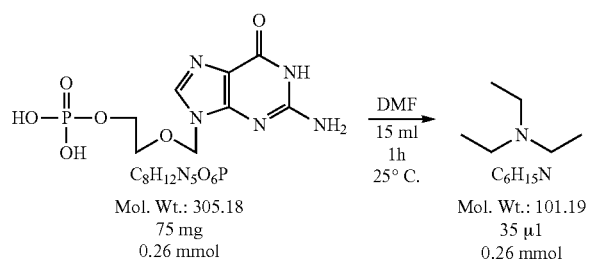
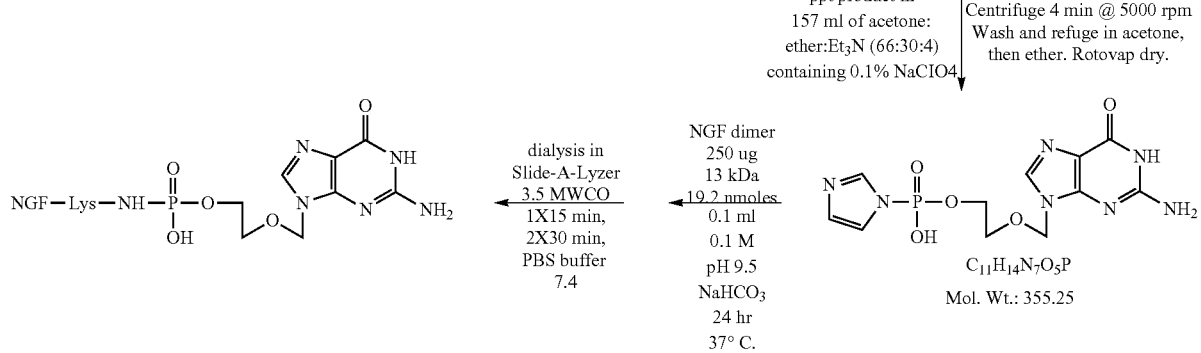

10. Examples of Human Neurotrophins as the Binding Agent (B)

Table 5 lists the amino acid sequences of human neurotrophins (NGF, BDNF, NT-3, and NT-4) that are used as the binding agent (B) of the present invention. Lysine residues that may be used to attach to the linker (L) which in turn is conjugated with the moiety (M) (which can be a therapeutic moiety or an imaging moiety) are highlighted and underlined in Table 5.

In general, it is preferred that the residue to which the linker is attached is one that is outside of the area of the protein that binds to the corresponding receptor. For example, the lysine at residue 95 is within the TrkA binding site, and thus is less preferred for attachment of a linker.

Preferably, where the binding agent B is NGF or BDNF, the linker is attached to the lysine residue at position 74 in the protein.

TABLE 5

Sequences of Examples of Human Neurotrophins

```
NERVE GROWTH FACTOR (NGF) (SEQ ID NO: 1):
  1 SER SER SER HIS PRO ILE PHE HIS ARG GLY GLU
    PHE SER VAL CYS ASP SER VAL SER VAL TRP VAL
    GLY ASP LYS THR THR ALA THR ASP ILE LYS GLY
    LYS GLU VAL MET VAL LEU GLY GLU VAL ASN ILE
    ASN ASN SER VAL PHE LYS GLN TYR PHE PHE GLU
    THR LYS CYS ARG ASP PRO ASN PRO VAL ASP SER
    GLY CYS ARG GLY ILE ASP SER LYS* HIS TRP ASN
    SER TYR CYS THR THR THR HIS THR PHE VAL LYS
    ALA LEU THR MET ASP GLY LYS GLN ALA ALA TRP
    ARG PHE ILE ARG ILE ASP THR ALA CYS VAL CYS
120 VAL LEU SER ARG LYS ALA VAL ARG ARG ALA
```

TABLE 5-continued

Sequences of Examples of Human Neurotrophins

```
BRAIN DERIVED NEUROTROPHIC FACTOR (BDNF)
(SEQ ID NO: 2):
  1 HIS SER ASP PRO ALA ARG ARG GLY GLU LEU SER
    VAL CYS ASP SER ILE SER GLU TRP VAL THR ALA
    ALA ASP LYS LYS THR ALA VAL ASP MET SER GLY
    GLY THR VAL THR VAL LEU GLU LYS VAL PRO VAL
    SER LYS GLY GLN LEU LYS GLN TYR PHE TYR GLU
    THR LYS CYS ASN PRO MET GLY TYR THR LYS GLU
    GLY CYS ARG GLY ILE ASP LYS* ARG HIS TRP ASN
    SER GLN CYS ARG THR THR GLN SER TYR VAL ARG
    ALA LEU THR MET ASP SER LYS LYS ARG ILE GLY
    TRP ARG PHE ILE ARG ILE ASP THR SER CYS VAL
119 CYS THR LEU THR ILE LYS ARG GLY ARG

NEUROTROPHIN-3 (NT-3) (SEQ ID NO: 3):
  1 TYR ALA GLU HIS LYS SER HIS ARG GLY GLU TYR
    SER VAL CYS ASP SER GLU SER LEU TRP VAL THR
    ASP LYS SER SER ALA ILE ASP ILE ARG GLY HIS
    GLN VAL THR VAL LEU GLY GLU ILE LYS THR GLY
    ASN SER PRO VAL LYS GLN TYR PHE TYR GLU THR
    ARG CYS LYS GLU ALA ARG PRO VAL LYS ASN GLY
    CYS ARG GLY ILE ASP ASP LYS HIS TRP ASN SER
    GLN CYS LYS THR SER GLN THR TYR VAL ARG ALA
    LEU THR SER GLU ASN ASN LYS LEU VAL GLY TRP
    ARG TRP ILE ARG ILE ASP THR SER CYS VAL CYS
119 ALA LEU SER ARG LYS ILE GLY ARG THR

NEUROTROPHIN-4 (NT-4) (SEQ ID NO: 4):
  1 GLY VAL SER GLU THR ALA PRO ALA SER ARG ARG
    GLY GLU LEU ALA VAL CYS ASP ALA VAL SER GLY
    TRP VAL THR ASP ARG ARG THR ALA VAL ASP LEU
    ARG GLY ARG GLU VAL GLU VAL LEU GLY GLU VAL
    PRO ALA ALA GLY GLY SER PRO LEU ARG GLN TYR
    PHE PHE GLU THR ARG CYS LYS ALA ASP ASN ALA
    GLU GLU GLY GLY PRO GLY ALA GLY GLY GLY GLY
    CYS ARG GLY VAL ASP ARG ARG HIS TRP VAL SER
    GLU CYS LYS ALA LYS GLN SER TYR VAL ARG ALA
```

TABLE 5-continued

Sequences of Examples of Human Neurotrophins

```
    LEU THR ALA ASP ALA GLN GLY ARG VAL GLY TRP
    ARG TRP ILE ARG ILE ASP THR ALA CYS VAL CYS
130 THR LEU LEU SER ARG THR GLY ARG ALA
```

*residue 74

11. Conjugates

Table 6 lists exemplary conjugation products indicative of the present invention and is not intended to be exhaustive, organized by type of linker chemistry; the structures of some of the various therapeutic moieties follows thereafter. NT=member of the neurotrophin family (e.g., NGF, BDNF, NT-3, NT-4, NT-6), with NGF and BDNF being of particular interest.

TABLE 6

| Functional Group | OH | OH | OH | COOH or $SO_3H$ | $NH_2$ |
|---|---|---|---|---|---|
| Neurotrophin | NT | NT | Thiolated NT | NT | Thiolated NT |
| Chemistry | $POCl_3$/IM | EDC or CDI | PMPI | EDC or CDI | EMCS or Sulfo-EMCS |
| Drug | Acyclovir (Anti-viral) | Acyclovir (Anti-viral) | Acyclovir (Anti-viral) | Etodolac (COX2 Inhibitor) | Tranylcypromine (MAOI) |
| | Ganciclovir (Anti-viral) | Ganciclovir (Anti-viral) | Ganciclovir (Anti-viral) | Meclofenamate (COX1&2, 5-LOX-inhibitor) | Propoxycaine ($Na^+$ channel blocker) |
| | Dexamethasone (Steroid) | Dexamethasone (Steroid) | Dexamethasone (Steroid) | Tauroursodeoxy-cholic Acid (Anti-oxidant) | |
| | Flumethasone (Steroid) | Flumethasone (Steroid) | Flumethasone (Steroid) | N-Acetyl-Cysteine (Anti-oxidant) | Procaine ($Na^+$ channel blocker) |
| | Piroxicam (COX1&2 inhibitor) | Piroxicam (COX1&2 inhibitor) | Piroxicam (COX1&2 inhibitor) | N-Acetyl-Aspartic Acid (Myelin Lipid Acylator) | |
| | Phentolamine (alpha Adrenergic antagonist) | Phentolamine (alpha Adrenergic antagonist) | Phentolamine (alpha Adrenergic antagonist) | Creatine (Mitochondrial Modulator) | Mexilitine ($Na^+$ channel blocker) |
| | Minocycline (Anti-bacterial) | Minocycline (Anti-bacterial) | Minocycline (Anti-bacterial) | Creatine Phosphate (Mitochondrial Energetic) | Gabapentin ($Na^+$, $Ca^{2+}$ channel blocker) |
| | Hyoscyamine (Anti-cholinergic) | Hyoscyamine (Anti-cholinergic) | Hyoscyamine- (Anti-cholinergic) | Ceftriaxone (Anti-bacterial) | Baclofen ($Ca^{2+}$ channel blocker) |
| | Zidovudine (AZT) (Anti-retroviral) | Zidovudine (AZT) (Anti-retroviral) | Zidovudine (AZT) (Anti-retroviral) | | Ketamine (NMDA antagonist) |
| | Lamivudine (3TC) (Anti-retroviral) | Lamivudine (3TC) (Anti-retroviral) | Lamivudine (3TC) (Anti-retroviral) | | Phenformin (NMDA channel subunit modifier) |
| | Enviroxime (Anti-enteroviral) | Enviroxime (Anti-enteroviral) | Enviroxime- (Anti-enteroviral) | | Pentamidine (Anti-infective) |
| | Adenosine (Adenosine receptor agonist) | Adenosine (Adenosine receptor agonist) | Adenosine- (Adenosine receptor agonist) | | Eflorinithine (Anti-infective) |
| | WHI-P131-* (JAK3 inhibitor) | WHI-P131 (JAK3 inhibitor) | WHI-P131- (JAK3 inhibitor) | | |
| Fluorescent Dyes | Alexa Fluor 488 succinimidyl ester- (Fluorescent probe) | Alexa Fluor 488 succinimidyl ester- (Fluorescent probe) | Alexa Fluor 488 $C_5$ maleimide- (Fluorescent probe) | | |
| | Alexa Fluor 647 succinimidyl ester- (Fluorescent probe) | Alexa Fluor 647 succinimidyl ester- (Fluorescent probe) | Alexa Fluor 647 $C_5$ maleimide- (Fluorescent probe) | | |

*WHI-P131 is also know as 4-(4'Hydroxyphenyl)-amino-6,7-dimethoxyquinazoline (WHI-P131). For a description of WHI-P131 and its uses, see, e.g., Uckun et al. Blood. 2002 Jun 1; 99(11): 4192-9.

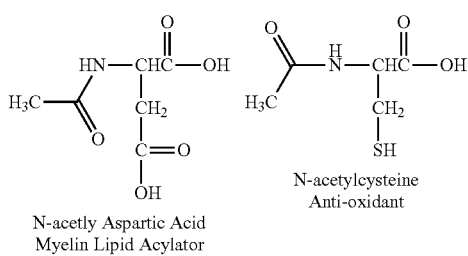

N-acetly Aspartic Acid
Myelin Lipid Acylator

N-acetylcysteine
Anti-oxidant

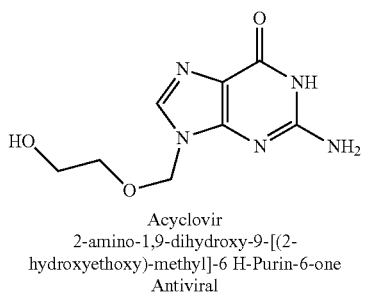

Acyclovir
2-amino-1,9-dihydroxy-9-[(2-hydroxyethoxy)-methyl]-6 H-Purin-6-one
Antiviral

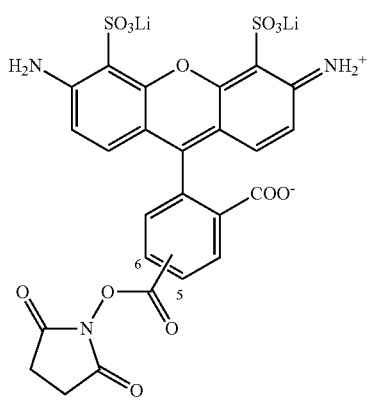

Alexa Fluor 488 carboxylic acid,
succinimidyl ester, dilithium salt
Fluorescent dye The Alexa Fluor dyes are available from Molecular Probes Inc., Eugene Oreg.

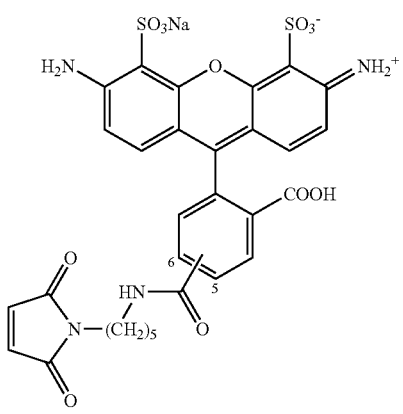

Alexa Flour 488 $C_5$ maleimide, sodium salt
Fluorescent dye

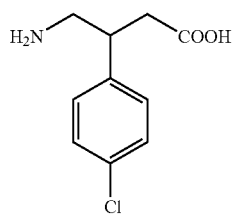

Baclofen
4-Amino-3-(4-chlorophenyl)-butanoic acid
Relaxant (muscle)
$Ca^{2+}$ channel blocker

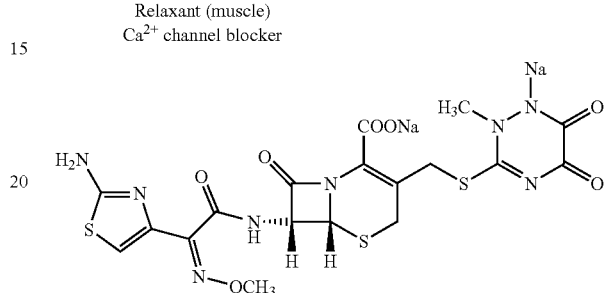

Ceftriaxone Sodium
7-[[2-amino-4-thiazoyl)(methoxyimino)acetyl]-amino]8-oxo-3-[[(1,2,5,6-tetrahydro-2methyl-5,6-dioxo-1,2,4-triazin-3yl)thio]methyl]-5-thia-1azabicyclo[4.2.0]oct-2-ene-2-carboxylic acid disodium salt
Anti-bacterial

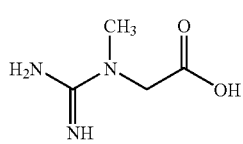

Creatine
Mitochondrial modulator

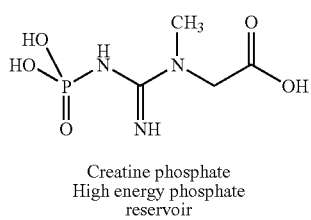

Creatine phosphate
High energy phosphate reservoir

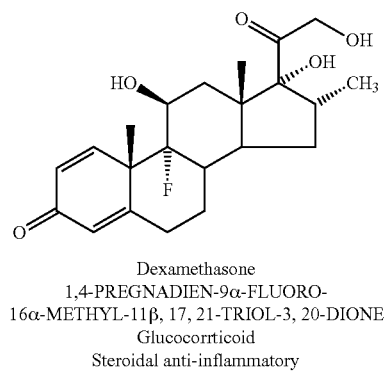

Dexamethasone
1,4-PREGNADIEN-9α-FLUORO-16α-METHYL-11β, 17, 21-TRIOL-3, 20-DIONE
Glucocorrticoid
Steroidal anti-inflammatory

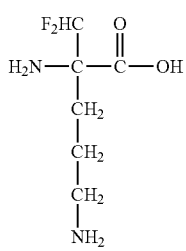

Eflornithine
2-(Difluorometyl)-DL-ornithine
Anti-infective

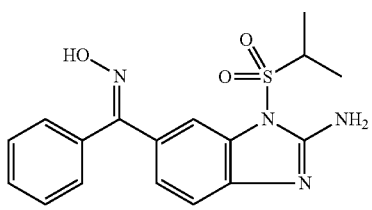

Enviroxime
6-[(Hydroxyimino)phenyl-methyl]-1-[(1-methylethyl)sulfonyl]-1H-benzinidazol-2-amine
Anti-enteroviral

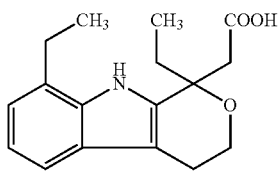

Etodolac
1,8-diethyl-1,3,4,9-tetrahydro-pyrano[3,4-b]indole-1-acetic acid
NSAID-COX2

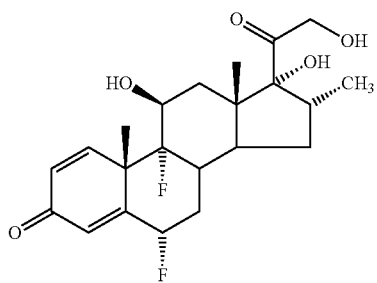

Flumethasone
1,4-PREGNADIEN-6α, 9α-DIFLUORO-16α-METHYL-11β, 17, 21-TRIOL-3, 20-DIONE
Glucocorticoid
Steroidal anti-inflammatory

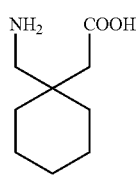

Gabapentin
1-(Aminomethyl)-cyclohexaneacetic acid
Anticonvulsant
$Na^+$, $Ca^{2+}$ channel blocker

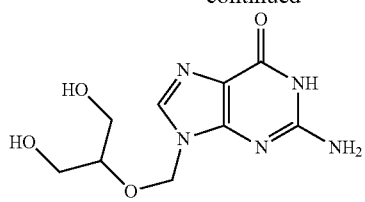

Ganciclovir
2-amino-1,9-dihydro-9-[[2-hydroxy-1-(hydroxymethyl)ethoxy]methyl]-6H-purin-6-one
Antiviral

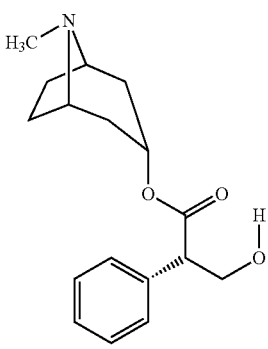

Hyoscyamine
α-(Hydroxymethyl)-benzeneacetic acid 8-methyl-8-azabicyclo[3.2.1]oct-3-yl ester
Anticholinergic

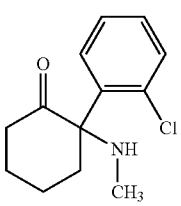

Ketamine
2-(2-Chlorophenyl)-2-(methylamino)-cyclohexanone
Anesthetic
NMDA antagonist

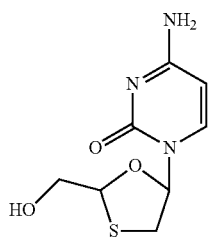

Lamivudine (3TC)
(2R-cis)-4-amino-1-1[2-hydroxymethyl)-1,3-oxathiolan-5-yl]-2(1H)-pyridinone
Anti-retroviral -continued

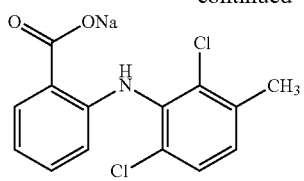

Meclofenamate Sodium
2-[(2,6-dichloro-3-methylphenyl)amino]-
benzoic acid monosodium salt
NSAID-COX1, COX2, 5-LOX

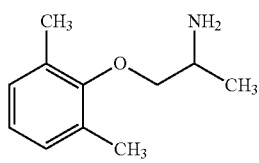

Mexilitine
1-(2,6-dimethylphenoxy)-2-propanamine
Cardiac depressant (anti-arrhythmic)

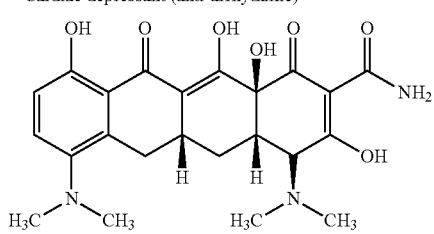

Minocycline
4,7-bis(dimethylamino)-1,4,4a,5,5a,6,11,12a-
octahydro-3,10,12,12a-tetrahydroxy-1,11-dioxo-2-
naphthacenecarboxamide
Anti-bacterial anti-oxidant

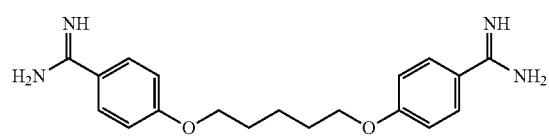

Pentamidine
4,4'-(Pentamethlenedioxy)dibenzamidine
Anti-infective

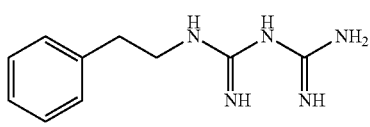

Phenformin
N-(2-phenylethyl)-
imidodicarbonimidic diamide
NMDA channel subunit modifier

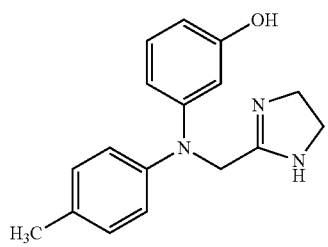

Phentolamine
3-[[(4,5-Dihydro-1H-imidazol-2-
yl)methyl](4-methylphenyl-amino]-phenol
α-adrenoceptor antagonist -continued

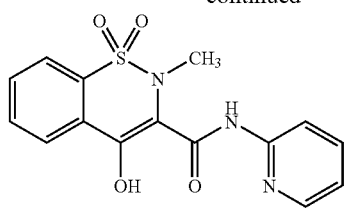

Piroxicam
4-Hydroxy-2-methyl-N-2-pyridinyl-2H-1,2-
benzothiazine-3-carboxamide 1, 1-dioxide
NSAID-COX1, COX2

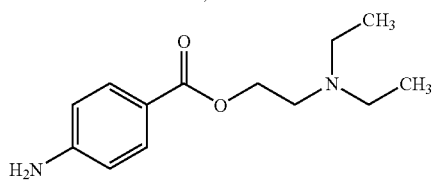

Procaine
2-(Diethylamino)ethyl p-aminobenzoate
Local anesthetic

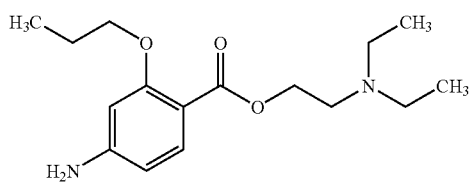

Propoxycaine
2-(Diethylamino)ethyl 4-amino-2-propoxybenzoate
Local anesthetic

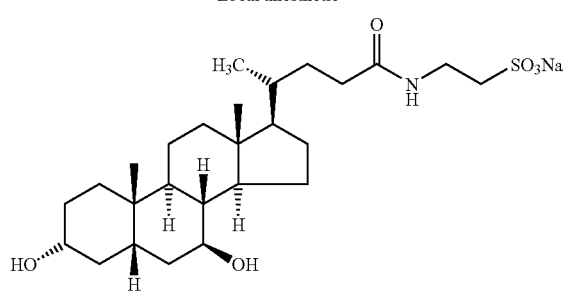

Taurousodeoxycholic Acid Sodium Salt
Bile acid anti-oxidant

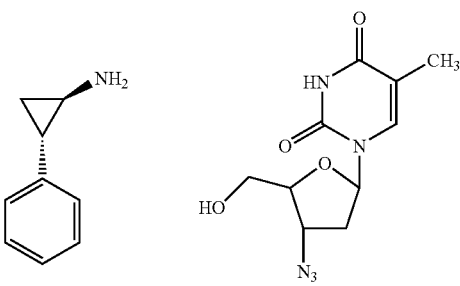

Tranylcypromine
(+/-)-trans-2-
Phenylcyclopropylamine
MAO Inhibitor

Zidovudine
3'-Azido-3'-deoxy-thymidine
Anti-retroviral

12. Methods for Using Compounds of the Present Invention

Described below are several methods for formulating and administering the compounds of the present invention. The compounds of the present invention may be employed in these and other applications.

a. Pharmaceutical Formulations Utilizing Compositions of the Present Invention

The compounds of the present invention may be incorporated into a variety of pharmaceutical compositions including, but not limited to: a sterile injectable solution or suspension; hard or soft gelatin capsules; tablets; emulsions; aqueous suspensions, dispersions, and solutions; suppositories. In general, the conjugate is formulated with an appropriate pharmaceutically acceptable carrier, and, where desired, with other additives such as stabilizers, buffers, and the like.

Other pharmaceutically suitable formulations for delivering the compounds of the present invention to nerve cells may also be used and are intended to fall within the scope of the present invention.

b. Routes of Administration

The compounds according to the present invention can be administered orally, by subcutaneous or other injection, intravenously, intracerebrally, intramuscularly, parenterally, transdermally, nasally or rectally. The form in which the compound is administered depends at least in part on the route by which the compound is administered.

While the present invention is disclosed with reference to preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. The patents, papers, and books cited in this application are to be incorporated herein in their entirety.

What is claimed is:

1. A conjugated 21-hydroxy steroid wherein a conjugate group pends from a steroid 21 hydroxyl group, and wherein the conjugate group comprises a brain-derived neurotrophic factor (BDNF) or BDNF receptor-binding fragment thereof.

2. The conjugated steroid of claim 1, having a 21-carbamate linkage to the conjugate group.

3. The conjugated steroid of claim 1, having a 21-phosphoramide linkage to the conjugate group.

4. The conjugated steroid of claim 1, wherein the BDNF or BDNF receptor-binding fragment pends covalently through an epsilon amino group of a lysine residue.

5. The conjugated steroid of claim 1, wherein the conjugate group comprises a brain-derived neurotrophic factor (BDNF) or BDNF fragment which binds to trkB receptors and is capable of being internalized therewith.

6. The conjugated steroid of claim 5, wherein the steroid is a corticosteroid.

7. The conjugated steroid of claim 6, wherein the corticosteroid is triamcinolone acetonide.

8. The conjugated steroid of claim 7, in which triamcinolone acetonide is conjugated by a 21-carbamate linkage to the BDNF, which pends covalently through an epsilon amino group of a lysine residue.

9. The conjugated steroid of claim 6, wherein the corticosteroid is fluocinolone acetonide.

10. The conjugated steroid of claim 9, in which fluocinolone acetonide is conjugated by a 21-carbamate linkage to the BDNF, which pends covalently through an epsilon amino group of a lysine residue.

11. The conjugated steroid of claim 6, wherein the corticosteroid is betamethasone.

12. The conjugated steroid of claim 11, in which betamethasone is conjugated by a 21-phosphoramide linkage to the BDNF, which pends covalently through an epsilon amino group of a lysine residue.

13. The conjugated steroid of claim 6, wherein the corticosteroid is dexamethasone.

14. The conjugated steroid of claim 13, in which dexamethasone is conjugated by a 21-phosphoramide linkage to the BDNF, which pends covalently through an epsilon amino group of a lysine residue.

15. The conjugated steroid of claim 1, wherein the steroid is a corticosteroid.

16. The conjugated steroid of claim 15, wherein the corticosteroid is triamcinolone acetonide.

17. The conjugated steroid of claim 16, in which triamcinolone acetonide is conjugated by a 21-carbamate linkage to a brain-derived neurotrophic factor (BDNF) or a receptor-binding fragment of BDNF, which pends covalently through an epsilon amino group of a lysine residue.

18. The conjugated steroid of claim 15, wherein the corticosteroid is fluocinolone acetonide.

19. The conjugated steroid of claim 18, in which fluocinolone acetonide is conjugated by a 21-carbamate linkage a brain-derived neurotrophic factor (BDNF) or a receptor-binding fragment of BDNF, which pends covalently through an epsilon amino group of a lysine residue.

20. The conjugated steroid of claim 15, wherein the corticosteroid is betamethasone.

21. The conjugated steroid of claim 20, in which betamethasone is conjugated by a 21-phosphoramide linkage to a brain-derived neurotrophic factor (BDNF) or a receptor-binding fragment of BDNF, which pends covalently through an epsilon amino group of a lysine residue.

22. The conjugated steroid of claim 20, in which betamethasone is conjugated by a 21-carbamate linkage to a brain-derived neurotrophic factor (BDNF) or a receptor-binding fragment of BDNF, which pends covalently through an epsilon amino group of a lysine residue.

23. The conjugated steroid of claim 15, wherein the corticosteroid is dexamethasone.

24. The conjugated steroid of claim 23, in which dexamethasone is conjugated by a 21-phosphoramide linkage to a brain-derived neurotrophic factor (BDNF) or a receptor-binding fragment of BDNF, which pends covalently through an epsilon amino group of a lysine residue.

25. The conjugated steroid of claim 23, in which dexamethasone is conjugated by a 21-carbamate linkage to a brain-derived neurotrophic factor (BDNF) or a receptor-binding fragment of BDNF, which pends covalently through an epsilon amino group of a lysine residue.

26. The conjugated steroid of claim 15, wherein the corticosteroid is cortisone.

27. The conjugated steroid of claim 26, in which cortisone is conjugated by a 21-carbamate linkage to a brain-derived neurotrophic factor (BDNF) or to a receptor-binding fragment of BDNF, which pends covalently through an epsilon amino group of a lysine residue.

28. A method of administering a steroid to a subject, the method comprising:
    injecting into a subject the conjugated 21-hydroxy steroid of claim 1 in an amount effective to treat pain.

* * * * *

SEQUENCE LISTING

```
<160> NUMBER OF SEQ ID NOS: 4

<210> SEQ ID NO 1
<211> LENGTH: 120
<212> TYPE: PRT
<213> ORGANISM: Homo sapiens

<400> SEQUENCE: 1

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 2
<211> LENGTH: 119
<212> TYPE: PRT
<213> ORGANISM: Homo sapiens

<400> SEQUENCE: 2

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
            35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80
```

```
Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 3
<211> LENGTH: 119
<212> TYPE: PRT
<213> ORGANISM: Homo sapiens

<400> SEQUENCE: 3

Tyr Ala Glu His Lys Ser His Arg Gly Glu Tyr Ser Val Cys Asp Ser
 1               5                  10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115

<210> SEQ ID NO 4
<211> LENGTH: 130
<212> TYPE: PRT
<213> ORGANISM: Homo sapiens

<400> SEQUENCE: 4

Gly Val Ser Glu Thr Ala Pro Ala Ser Arg Arg Gly Glu Leu Ala Val
 1               5                  10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
        35                  40                  45

Gly Ser Pro Leu Arg Gln Tyr Phe Phe Glu Thr Arg Cys Lys Ala Asp
    50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
   130
```